(12) United States Patent
Suzuki et al.

(10) Patent No.: US 7,320,794 B2
(45) Date of Patent: Jan. 22, 2008

(54) TRANSPORTER PROTEIN

(75) Inventors: Shunichi Suzuki, Kawasaki (JP); Kenzo Yokozeki, Kawasaki (JP); Peter Henderson, Leeds (GB)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/276,614

(22) Filed: Mar. 8, 2006

(65) Prior Publication Data
US 2006/0183190 A1 Aug. 17, 2006

(51) Int. Cl.
- *A61K 39/00* (2006.01)
- *A61K 39/38* (2006.01)
- *C12P 1/00* (2006.01)
- *C12P 21/06* (2006.01)
- *C07K 1/00* (2006.01)
- *C07H 21/04* (2006.01)

(52) U.S. Cl. ............... 424/185.1; 424/184.1; 424/190.1; 424/200.1; 424/234.1; 424/257.1; 435/41; 435/69.1; 435/71.1; 435/440; 435/471; 435/476; 530/300; 530/350; 536/23.1; 536/23.7

(58) Field of Classification Search ............ 424/184.1, 424/185.1, 190.1, 200.1, 234.1, 257.1; 435/41, 435/69.1, 71.1, 440, 471, 476; 530/300, 530/350; 536/23.1, 23.7
See application file for complete search history.

(56) References Cited

U.S. PATENT DOCUMENTS

2003/0109013 A1  6/2003  Takenaka et al.

FOREIGN PATENT DOCUMENTS

| EP | 1 188 826 | 3/2002 |
|----|-----------|--------|
| JP | 2002-013552 | 1/2002 |
| WO | WO99/51722 | 10/1999 |
| WO | WO01/23582 | 4/2001 |
| WO | WO02/072841 | 9/2002 |

OTHER PUBLICATIONS

Sumrada, R., et al., "Allantoin Transport in *Saccharomyces cerevisiae*," J. Bacteriol. 1977;131(3):839-847.
Watanabe, K., et al., "Cloning and Sequencing of the Gene Involved in the Conversion of 5-Substituted Hydantoins to the Corresponding L-Amino Acids from the Native Plasmid of *Pseudomonas* sp. Strain NS671," J. Bacteriol. 1992;174(3):962-969.
Wiese, A., et al., "Organization of gene responsible for the stereospecific conversion of hydantoins to α-amino acids in *Arthrobacter aurescens* DSM 3747," Arch. Microbiol. 2001;176:187-196.
Wilms, B., et al., "Development of an *Escherichia coli* whole cell biocatalyst for the production of L-amino acids," J. Biotechnol. 2001;86:19-30.
International Search Report for PCT Appl. No. PCT/JP2004/013066 (Dec. 28, 2004).

*Primary Examiner*—Rodney P Swartz
(74) *Attorney, Agent, or Firm*—Shelly Guest Cermak; Cermak Kenealy & Vaidya LLP

(57) ABSTRACT

A novel protein which has an activity to transport hydantoin compounds is described, as well as a recombinant expressing this transporter protein. From *Microbacterium liquefaciens* strain AJ3912, a novel gene was discovered to encode a protein which is able to transport hydantoin compounds. A recombinant with an excellent ability to uptake hydantoin compounds is obtained by introducing and expressing the novel gene, called mhp, using gene recombination techniques.

18 Claims, 9 Drawing Sheets

*Microbacterium liquefaciens* AJ3912

(A) SDS-PAGE, (B) Western Blotting
lane 1; Molecular weight marker, lane2, 3; Total membrane fraction (lane2; uninduced, lane 3; induced), lane 4; Cytosolic fraction, lane 5; Inner membrane fraction; lane 6; Outer membrane fraction, lane 7; Solubilized fraction, lane 8; Unsolubilized fraction, lane 9; purified MHP

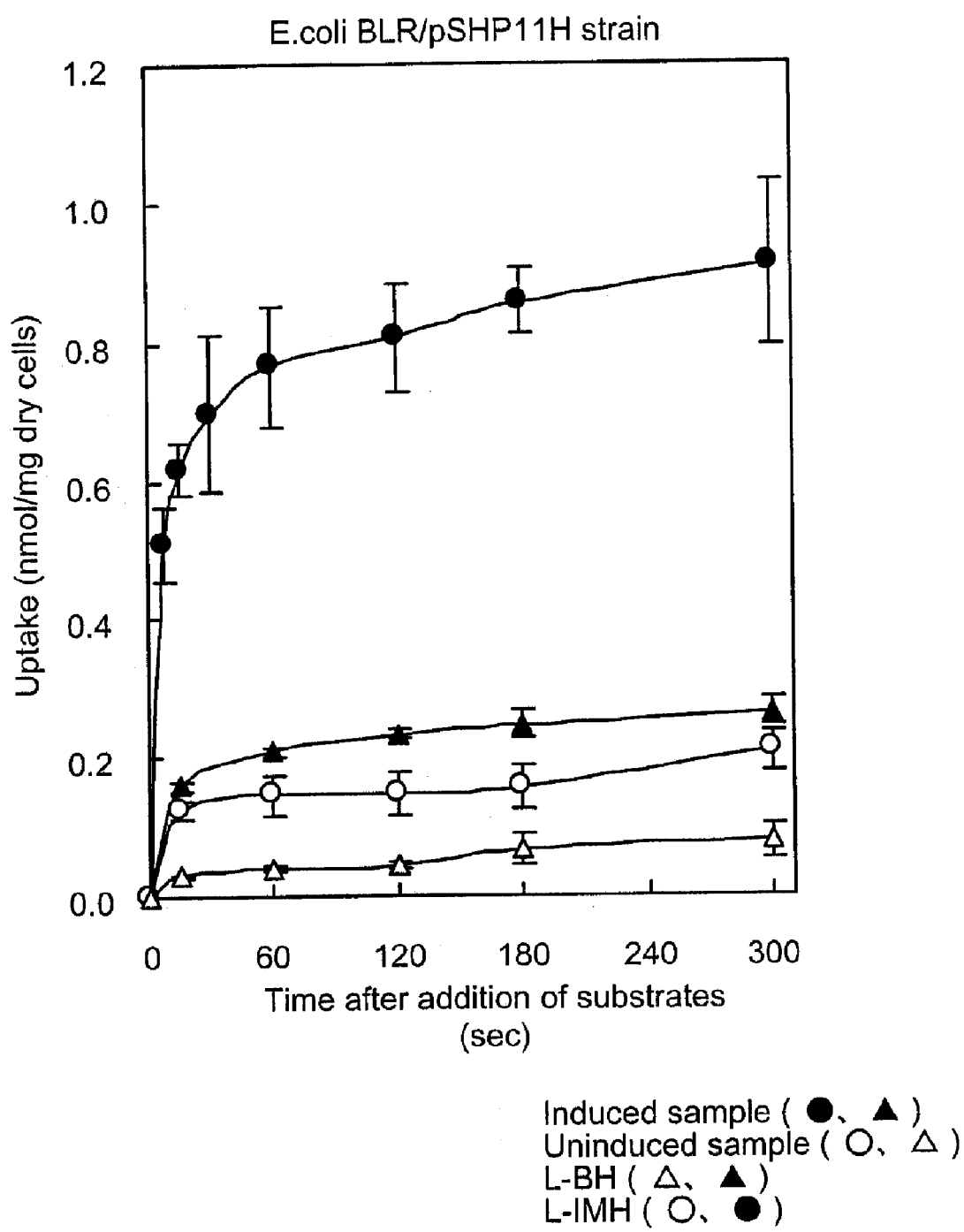

Time after the addition of substrates (min)

Induced sample ( ●、▲、■ )
Uninduced sample ( ○、△、□ )
Sodium ion added ( △、▲ )
Control ( ○、● )
DNP added ( □、■ )

TRANSPORTER PROTEIN

This application claims priority under 35 U.S.C. §119(a) to JP2003-315306, filed Sep. 8, 2003, and under 35 U.S.C. §120 to PCT/JP2004/13066, filed Sep. 8, 2004, the entireties of which are incorporated by reference. The Sequence Listing on Compact Disk filed herewith is also hereby incorporated by reference in its entirety (File Name: US-278 Seq List; File Size: 24 KB; Date Created: Mar. 8, 2006).

BACKGROUND OF THE INVENTION

1. Field of the Invention

The present invention relates to a novel transporter protein which has a transporter activity for a hydantoin compound.

2. Brief Description of the Related Art

One of the known methods for producing amino acids using an enzyme is to asymmetrically decompose a 5-substituted hydantoin compound, which is inexpensive to chemically synthesize, to an optically active amino acid. This method for producing optically active amino acids from the 5-substituted hydantoin compound has a widespread importance in preparing medicines, chemical products, food additives, and the like.

The 5-substituted hydantoin compound is converted to an amino acid by a hydrolysis reaction using enzymes (A) and (B) as shown in the following Reaction Formula (I).

(A) An enzyme which catalyzes a hydrolytic reaction of the 5-substituted hydantoin compound to produce an N-carbamylamino acid (hydantoinase, hereinafter referred to as 'HHase').

(B) An enzyme which catalyzes a hydrolytic reaction of the produced N-carbamylamino acid to produce an optically active amino acid (N-carbamylamino acid hydrolase, hereinafter referred to as 'CHase'. Generally, carbamylamino acid hydrolase may be also referred to as carbamylase).

To produce an optically active amino acid from a 5-substituted hydantoin compound, an optically specific enzyme may be used, such as (A) hydantoinase and (B) N-carbamylamino acid hydrolase, as follows.

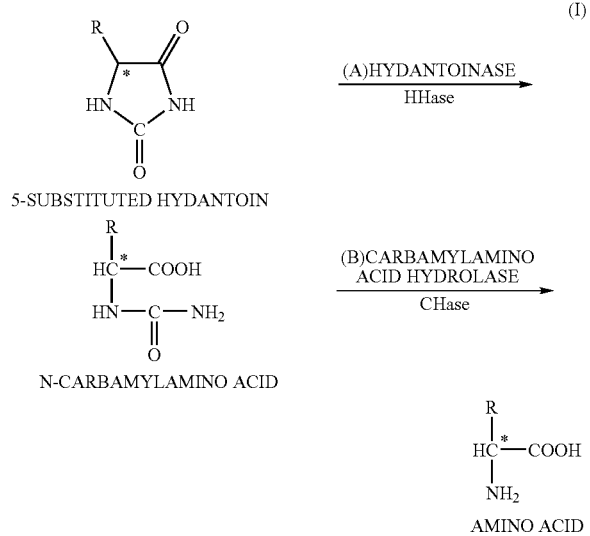

Known methods for producing an optically active amino acid from a 5-substituted hydantoin compound typically use a microbial enzyme. Other known methods use a combination of a microbial enzyme and a specific chemical reaction. A method for producing amino acids on a large industrial scale using a microorganism or a transformant producing the above-described enzymes (A) and (B) is commonly used. However, in these methods, most of the enzymes which catalyze the reaction are in the cell. Thus, if a substrate has a poor membrane permeability, it cannot reach the enzyme in the cell, which may cause a problem in that the 5-substituted hydantoin compound cannot be effectively converted into the optically active amino acid. To resolve this problem, the cells need to be disrupted before the reaction to solubilize the enzyme. However, disrupting cells in industrial production is complicated. Furthermore, insoluble substances which are generated by the disrupting process possibly may prohibit product recovery after the reaction.

SUMMARY OF THE INVENTION

It is an object of the present invention to provide a method for improving the membrane permeability of a substrate. To this end, a microorganism or a transformant which produces the above-described enzymes (A) and (B) may be imparted with an ability to express a transporter for the hydantoin compound (the substrate) by a genetic recombination. The transporter is a type of protein which participates in the transportation of substances. Most of the transporters exist on the biomembrane as a membrane protein which transport specific substances across the membrane. Since the transporters are involved in such a transfer of substances, the properties of the cell relating to transportation of the substances can be modified by modifying the expression of transporter genes. In other words, in a bioconversion process using intact cells and substrates with poor membrane permeability, introducing a hydantoin transporter protein may result in an efficient uptake of the substrate.

However, handling of membrane proteins (purification, function analysis, large-scale expression and the like) is difficult compared to soluble proteins. Therefore, research to identify such transporters has not advanced compared to that for the soluble proteins, and many genes encoding transporters are still unknown.

If an amino acid sequence and a base sequence of the transporter for the hydantoin compound can be determined and expressed by genetic recombination, the 5-substituted hydantoin compound could be effectively taken up into the cell. Thereby, a disruption or bacteriolysis treatment process to extract the enzymes from the cell would become unnecessary, and consequently the production process could be simplified.

There have been no reports about transporters for 5-substituted hydantoin compounds, except for one on the transporter of allantoin which has the structure of 5-ureidohydantoin (Sumrada, et al., J. Bacteriol. 131: 839-847 (1977)). Therefore, a novel hydantoin transporter is needed in the production process of an optically active amino acid from hydantoin.

Genes encoding a transporter homologue protein in the vicinity of genes encoding a hydantoinase, carbamoylase, or hydantoin racemase have been disclosed. However, the functions thereof have not been determined as yet.

Therefore, an object of the present invention is to provide a novel transporter protein having a transporter activity for a hydantoin compound, and a transformant in which a hydantoin transporter DNA is expressed.

The present inventors have conducted extensive studies to resolve the above-described problems. As a result, a transporter homologue (MHP) of unknown function has been found among the gene family of 5-substituted hydantoin hydrolases in bacteria belonging to the genus *Microbacterium*, as well as a protein with transporter activity for the hydantoin compound.

In addition, the present inventors have constructed a transformant having the hydantoin transporter DNA incorporated thereinto, and determined that the transformant takes up the hydantoin compound effectively into cells.

That is, the present invention is as follows.

It is an object of the present invention to provide a protein comprising hydantoin-transporter activity for 5-substituted hydantoin compounds, except allantoin.

It is a further object of the present invention to provide the protein as described above, wherein said 5-substituted hydantoin compound comprises the following formula (1):

(1):

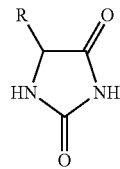

wherein R is selected from the group consisting of a $C_{1-8}$ straight or branched alkyl group, a $C_{2-8}$ straight or branched alkylene group, an aryl group or aralkyl group having 20 or less carbon atoms, a $C_{1-8}$ mercaptoalkyl group, and a $C_{2-8}$ alkylthioalkyl group.

It is a further object of the present invention to provide the protein as described above, wherein R is an aralkyl group having 20 or less carbon atoms.

It is a further object of the present invention to provide the protein as described above, wherein R is an indolylmethyl group or a benzyl group.

It is a further object of the present invention to provide the protein as described above, wherein the protein is derived from a microorganism belonging to the genus *Microbacterium*.

It is a further object of the present invention to provide the protein as described above, wherein the protein is derived from *Microbacterium liquefaciens*.

It is a further object of the present invention to provide the protein as described above, wherein the protein is derived from *Microbacterium liquefaciens* AJ3912.

It is a further object of the present invention to provide a protein having hydantoin-transporter activity, wherein the amino acid sequence of the protein is selected from the group consisting of:

(A) an amino acid sequence comprising the sequence set forth in SEQ ID No. 2, and (B) an amino acid sequence wherein, one or several amino acids are substituted, deleted, inserted, added and/or inverted in the amino acid sequence set forth in SEQ ID No. 2.

It is a further object of the present invention to provide the protein as described above, wherein the protein transports a hydantoin compound selected from the group consisting of 5-indolylmethyl hydantoin, 5-benzyl hydantoin, and combinations thereof.

It is a further object of the present invention to provide the protein as described above, wherein said hydantoin-transporter activity is selective for the L-isomer of a 5-substituted hydantoin compound.

It is a further object of the present invention to provide a DNA encoding a protein having a hydantoin-transporter activity, wherein the protein is selected from the group consisting of:

(A) an amino acid sequence comprising the sequence set forth in SEQ ID No. 2, and (B) an amino acid sequence wherein, one or several amino acids are substituted, deleted, inserted, added and/or inverted in the amino acid sequence set forth in SEQ ID No. 2.

It is a further object of the present invention to provide a DNA encoding a protein having a hydantoin-transporter activity, wherein the DNA is selected from the group consisting of:

(a) a DNA sequence comprising the sequence set forth in SEQ ID No. 1, and (b) a DNA sequence which hybridizes under stringent conditions with DNA comprising a DNA sequence which is complementary to the DNA sequence set forth in SEQ ID No. 1.

It is a further object of the present invention to provide a vector comprising the DNA as above.

It is a further object of the present invention to provide the vector as described above, wherein the vector is selected from the group consisting of pUC, pTTQ, and derivatives thereof.

It is a further object of the present invention to provide a cell which is transformed by the vector as described above.

It is a further object of the present invention to provide the cell as described above, wherein the cell is *Escherichia coli*.

It is a further object of the present invention to provide the cell as described above, wherein the *Escherichia coli* is *E. coli* BLR.

It is a further object of the present invention to provide a method for producing an amino acid comprising cultivating the cell as described above in a culture medium, and collecting the amino acid from the medium or the cell.

The hydantoin transporter of the present invention transports hydantoin compounds. If the transporter is present in a biomembrane, it mediates the passage of the hydantoin compounds through the biomembrane. Therefore, by expressing the present hydantoin transporter with gene recombination techniques, it becomes possible to construct a transformant which has an excellent ability of cellular uptake of the hydantoin compounds.

Conventionally, in order to take the enzymes produced by microorganisms out of the cells, it was necessary to solubilize the enzymes by disrupting the cells before carrying out the reactions. However, since the cells having the present hydantoin transporter can uptake the substrate hydantoin compounds into the cell efficiently, it becomes possible to perform enzymatic reactions efficiently within the cells. Accordingly, the disruption treatment process of the cells, which used to be necessary in the conventional method for taking the enzyme out of the cell, is no longer necessary.

BRIEF DESCRIPTION OF THE DRAWINGS

FIG. 5 illustrates the results of experiments measuring 5-substitued hydantoin uptake by intact cells of *E. coli* BLR/pSHP11H.

DETAILED DESCRIPTION OF EXEMPLARY EMBODIMENTS

The present invention will be explained in detail with reference to the drawings, in the following order:

[I] Hydantoin transporter.
(1) DNA encoding the hydantoin transporter,
(2) Properties of the hydantoin transporter,
[II] Preparation of the transformant in which the hydantoin transporter DNA is expressed.

[I] Hydantoin Transporter

A gene mhp, the function of which was unknown, was found within the gene family encoding hydantoin racemase (HRase), hydantoinase (HHase) and carbamylase (CHase), which act on a 5-substituted hydantoin compound in *Microbacterium liquefaciens* AJ 3912. It was determined that a protein encoded by the gene has a transporter activity for the hydantoin compound.

Figure 1:
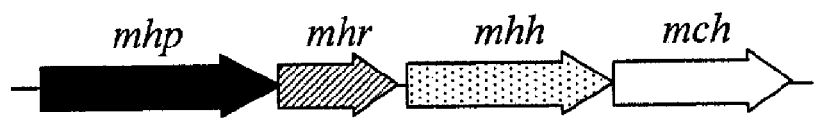
FIG. 1 shows the relative location of the gene family of hydantoin hydrolase for *Microbacterium liquefaciens* strain AJ3912.

FIG. 1 shows the relative location for the genes which are members of the gene family of hydantoin hydrolases of *Microbacterium liquefaciens* AJ3912. In FIG. 1, each gene is shown by an arrow which indicates the direction of translation. As shown in FIG. 1, the mhp gene, which encodes MHP, is upstream of mhr, mhh, and mch. These three downstream genes encode hydantoin racemase, hydantoinase and carbamylase, respectively, and all of which recognize the 5-substituted hydantoin as a substrate. Thus, it appears that these genes form an operon in which the expression is simultaneously regulated by the same promoter.

The hydantoin transporter of the present invention is a protein which transports the hydantoin compound. The transporter of the present invention is a membrane protein. If the transporter is present in a biomembrane, it mediates the passage of the hydantoin compounds through the biomembrane. The transporter of the present invention is assumed to transport the hydantoin compound by active transport, and thereby facilitates uptake of the hydantoin compound into the cells.

The hydantoin transporter of the present invention transfers a chemical substance which is different, in a strict sense, from an enzyme which catalyzes a chemical reaction. However, a transporter has similarities with such an enzyme. For example, the transporter has substrate specificity, i.e., it acts on specific chemical substances and transports them, and it can also be antagonized by analogues of the substrate. Therefore, chemical substances transported by the transporter are referred to as a "substrate", and the activity for transporting the hydantoin compound is referred to as a "hydantoin-transporter activity" in the present specification.

The activity of the hydantoin transporter can be measured by an uptake assay using intact cells. The uptake assay using intact cells may be carried out in accordance with the method of West, and Henderson (I. C. West (1970) Lactose transport coupled to proton movements in *Escherichia coli*, Biochem. Biophys. Res. Commun. 41: 655-661; P. J. F. Henderson and A. J. S. Macpherson (1986), Assay, genetics, proteins, and reconstitution of proton-linked galactose, arabinose, and xylose transport systems of *Escherichia coli*, Methods Enzymol. 125: 387-429).

Specifically, the uptake reaction may be carried out by adding an RI-labelled substrate ($^3$H-BH (benzyl hydantoin), $^3$H-IMH (indolylmethyl hydantoin)) to a suspension of the cells that express the hydantoin transporter. After initiating the reaction, sampling may be conducted at time intervals. Immediately after sampling, each aliquot may be collected by a filter of 0.45 μm pore size (preincubated in a washing liquid of 150 mM KCl, 5 mM MES (pH 6.6)) and washed thoroughly by the rinsing liquid. Thereafter, by measuring radioactivity remaining on the filter with a liquid scintillation counter, the substrate uptaken into the cells is quantified, and the hydantoin-transporter activity can be determined.

Weak activity can be distinguished from the background by using a control whereby cells are incubated under an uninduced condition in which the transporter gene is not expressed.

In the present invention, existence of the transporter activity is defined by the recognition of the substrate uptake into the cells in a solution for the reaction containing 25 μM substrate, at pH 6.6 at 25° C. After the initiation of the substrate uptake into the cells, the amount of the substrate in the cells usually continues to increase. However, after the lapse of a certain period of time, the substrate concentration in the cells reaches a saturation concentration and the uptake speed becomes equilibrated with the discharge speed. In the present invention, the amount of the substrate uptake observed in the saturation state is preferably 0.01 nmol/mg or higher, more preferably 0.1 nmol/mg or higher, per weight of the cells.

The DNA encoding the hydantoin transporter of the present invention is shown in SEQ ID No. 1. In addition, the amino acid sequence of the hydantoin transporter encoded by the base sequence of SEQ ID No. 1, is shown in SEQ ID No. 2.

(1) DNA Encoding the Hydantoin Transporter

The transporter gene of the present invention has the DNA sequence of SEQ ID No. 1, and can be isolated from the chromosomal DNA of *Microbacterium liquefaciens* AJ 3912 as described above. The DNA sequence of SEQ ID No. 1 is 82% homologous with a transporter homologue protein, HyuP, of unknown function encoded by a gene from the family of hydantoin hydrolase in *Arthrobacter aurescens* DSM 3747 (A. Wiese, C. Syldatk, R. Mattes, and J. Altenbuchner (2001) Organization of genes responsible for the stereospecific conversion of hydantoins to α-amino acids in *Arthrobacter aurescens* DSM3747, Arch. Microbiol. 176: 187-196). The DNA of SEQ ID No. 1 also is 31% homologous with a transporter homologue protein, ORF5 protein (P_ORF5), (K. Watabe, T. Ishikawa, Y. Mukohara, and H. Nakamura (1992) Cloning and sequencing of the genes involved in the conversion of 5-substituted hydantoins to the corresponding L-amino acid from the native plasmid of *Pseudomonas* sp. NS671, J. Bacteriol. 174: 962-969) of unknown function encoded by a gene from the family of hydantoin hydrolase genes in *Pseudomonas* sp. NS671.

Homology herein is calculated by setting parameters as defaults using the gene analysis software "FASTA" (Wisconsin-Madison Univ., USA).

A method for obtaining the DNA encoding the hydantoin transporter will now be explained.

The base sequence of the DNA is deduced on the basis of the amino acid sequence of the hydantoin transporter (SEQ ID No. 2) which was identified by the present inventors. Universal codons are used to deduce the base sequence of the DNA.

Based on the deduced DNA sequence, a DNA molecule of about 30 base pairs is synthesized. The method for synthesizing the DNA molecule is disclosed in Tetrahedron Letters, 22: 1859 (1981). In addition, the DNA molecule may be synthesized using a commercial synthesizer (Applied Biosystems Co., Ltd.). The DNA molecule may be used as a probe for isolating a full-length DNA encoding the hydantoin transporter from the chromosome gene library of hydantoin transporter-producing microorganisms. Alternatively, the DNA molecule may be used as a primer when the DNA encoding the transporter of the present invention is amplified by PCR. An example of the primer is shown in SEQ ID Nos. 5 and 6. Since the DNA obtained by PCR amplification may not include the full-length region of the DNA encoding the transporter, the DNA amplified by PCR may be used as a probe for isolating the full-length DNA from the chromosome gene library of the transporter-producing microorganisms.

The hydantoin transporter-producing microorganisms which are sources for obtaining the hydantoin transporter DNA may include any bacteria belonging to the genus *Microbacterium*, preferably *Microbacterium liquefaciens*, and more preferably *Microbacterium liquefaciens* AJ3912.

*Microbacterium liquefaciens* AJ3912 strain has been deposited as follows:

*Microbacterium liquefaciens* AJ3912 strain (i) Deposit No.: FERM BP-7643 (formerly FERM-P3133, changed on Jun. 27, 2001)

(ii) Deposit date: Jun. 27, 1975

(iii) Depository authority: International Patent Organism Depositary, National Institute of Advanced Industrial Science and Technology (Tsukuba Central 6, 1-1-1 Higashi, Tsukuba, Ibaraki, Japan)

The PCR procedure is described, for example, in White, T. J. et al., Trends Genet. 5, 185 (1989). The method for constructing the chromosomal DNA, and the method for isolating the desired DNA molecule from the gene library using a DNA molecule as a probe, are described, for example, in Molecular Cloning, 2nd edition, Cold Spring Harbor press (1989).

The method for determining the base sequence of the DNA encoding the isolated hydantoin transporter is described, for example, in A Practical Guide to Molecular Cloning, Chapters 9 and 11, John Wiley & Sons, Inc. (1985). In addition, the base sequence can be determined by using a DNA sequencer of Applied Biosystems Co., Ltd.

The DNA encoding the protein having the transporter activity for a hydantoin compound is not restricted to the DNA shown in SEQ ID No. 1. That is, differences in the base sequences are observed among bacteria belonging to the genus *Microbacterium* producing the hydantoin transporters, depending on species and strains.

In addition, the DNA of the present invention is not limited to the DNA encoding the isolated hydantoin transporter, but also of course includes the DNA obtained by artificially mutating a DNA encoding the hydantoin transporter that had been isolated from the chromosomal DNA of the hydantoin transporter-producing microorganism, as long as such a mutated DNA encodes the hydantoin transporter. Examples of the methods that are frequently used for such an artificial mutation may include a method of introducing site-specific mutation which is described in Kunkel, et al., Methods in Enzymology, 154: 367-382 (1987).

The DNA of the present invention may also include a DNA which hybridizes under a stringent condition with a DNA consisting of a base sequence complimentary to the base sequence described in SEQ ID No. 1, and encodes the protein having the hydantoin-transporter activity. "Stringent condition" herein means conditions under which so-called a specific hybrid is formed, and a non-specific hybrid is not formed. An example thereof may be the condition under which DNAs having high homology, for example 50% or higher, more preferably 80% or higher, further preferably 90% or higher, particularly more preferably, 95% or higher hybridize to each other, but DNA having homology lower than that level does not hybridize to each other. The conditions may also be defined by hybridization conditions at salt concentrations corresponding to 0.1×SSC, 0.1% SDS at 37° C., preferably 0.1×SSC, 0.1% SDS at 60° C., and further preferably 0.1×SSC, 0.1% SDS at 65° C., which are ordinary washing conditions of Southern hybridization. In addition, "hydantoin-transporter activity" herein means a transporter activity for at least one kind of hydantoin compound. However, the protein encoded by the base sequence which hybridizes under the stringent condition with the base sequence complimentary to the base sequence described in SEQ ID No. 1 may desirably have 10% or higher, preferably 30% or higher, more preferably 50% or higher, particularly more preferably 70% or higher of the hydantoin-transporter activity as compared with that of the protein having the amino acid sequence described in SEQ ID No. 2 under the conditions of 25° C. and pH 6.6 for 5-benzyl hydantoin.

Furthermore, the DNA of the present invention may also include the DNA encoding a protein which is substantially the same as the hydantoin transporter encoded by the DNA described in SEQ ID No. 1. That is, the DNA of the present invention may also include:

(a) the DNA encoding a protein consisting of the amino acid sequence described in SEQ ID No. 2; and (b) the DNA encoding a protein having an amino acid sequence that has substitution, deletion, insertion, or inversion of one or several amino acid residues in the amino acid sequence described in SEQ ID No. 2, and having the hydantoin-transporter activity.

"One or several" herein means the range of numbers of the amino acid residues which results in no major damage on the stereo-structure and the transporter activity of the protein, and may specifically be 1 to 50, preferably 1 to 30, and more preferably 1 to 10. "Hydantoin-transporter activity" herein means a transporter activity for at least one kind of the hydantoin compounds. However, the amino acid sequence having substitution, deletion, insertion, or inversion of one or several amino acid residues in the amino acid sequence described in SEQ ID No. 2 may desirably have 10% or higher, preferably 30% or higher, more preferably 50% or higher, and particularly more preferably 70% or higher hydantoin-transporter activity as compared with that of the protein having the amino acid sequence described in SEQ ID No. 2 under the condition of 25° C. and pH 6.6 for 5-benzyl hydantoin.

(2) Properties of the hydantoin transporter

The hydantoin transporter of the present invention typically has the amino acid sequence of SEQ ID No. 2 as clarified by the aforementioned gene isolation and analysis. However, the present invention may also include a protein having the amino acid sequence that has substitution, deletion, insertion, addition or inversion of one or several amino acid residues in the amino acid sequence described in SEQ ID No. 2, and having the hydantoin-transporter activity.

That is, the hydantoin transporter of the present invention also includes:

(a) a protein consisting of the amino acid sequence described in SEQ ID No. 2

(b) a protein having an amino acid sequence that has substitution, deletion, insertion, or inversion of one or several amino acid residues in the amino acid sequence described in SEQ ID No. 2, and having the hydantoin-transporter activity.

"One or several" and "hydantoin-transporter activity" herein are as described in the Item (1) "DNA encoding hydantoin transporter".

The hydantoin transporter of the present invention is a transporter which recognizes a 5-substituted hydantoin compound, except allantoin, as a substrate. The hydantoin transporter of the present invention may have transporter activity for a 5-substituted hydantoin compound that has a strong hydrophobic substituent on the 5-position carbon of the hydantoin ring, and more specifically, a 5-substituted hydantoin compound represented by the following formula (1).

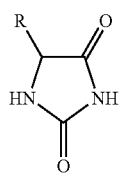
(1)

wherein R is a $C_{1-8}$ straight or branched alkyl group, a $C_{2-8}$ straight or branched alkylene group, an aryl group or aralkyl group having 20 or less carbon atoms, a $C_{1-8}$ mercaptoalkyl group, or a $C_{2-8}$ alkylthioalkyl group.

In the above-described formula (1), R is preferably a $C_{3-8}$ branched alkyl group, an aralkyl group having 20 or less carbon atoms, mercaptomethyl group or methyl thioethyl group, more preferably an aralkyl group having 20 or less carbon atoms, and particularly preferably indolylmethyl group or benzyl group. When R is indolylmethyl group or benzyl group, the 5-substituted hydantoin compound of the above-described Formula (1) is 5-indolylmethyl hydantoin or 5-benzyl hydantoin, respectively.

Subsequently, the enzymological and chemical properties of the hydantoin transporter of the present invention derived from *Microbacterium liquefaciens* AJ 3912 strain (hereinafter, it may be abbreviated as MHP) are described below.

It has been confirmed that MHP of the present invention may be expressed in the membrane fraction in *Escherichia coli*. It is assumed that MHP is localized specifically to the internal membrane. MHP of the present invention has a function of mediating passage of the hydantoin compound through the membrane when the MHP is present in the biomembrane.

MHP of the present invention has a transporter activity for a hydantoin compound, and especially has an excellent transporter activity for 5-indolylmethyl hydantoin and 5-benzyl hydantoin. In addition, MHP of the present invention has an optical selectivity for recognizing a substrate, and acts selectively on the L-isomer of the hydantoin compound. "Acting selectively on the L-isomer" herein means that the reaction with the L-isomer prevails when coexisting with the R-isomer. Specifically, if the amount of the L-isomer which is taken up into the cells is greater than that of the R-isomer when measured using the above-described intact cell uptake assay, the transporter is regarded as L-isomer selective.

MHP of the present invention may be active in a range of pH 4 to 10. The optimum pH thereof is in the neutral range of pH 6 to 8. MHP of the present invention is stable at the temperature of 30° C. or lower, and especially 25° C. or lower.

[II] Preparation of a Transformant in which the Hydantoin Transporter DNA is Expressed Subsequently, the method for producing the transformant of the present invention in which the hydantoin transporter DNA is expressed will be explained. There are many known examples of producing useful proteins, such as enzymes and physiologically active substances, using recombinant DNA techniques. By using such a recombinant DNA technique, useful proteins that are naturally present in a trace amount can be produced in large quantities.

The scheme of the production process for obtaining the transformant of the present invention will be explained. At first, the DNA encoding the hydantoin transporter of the present invention is prepared. Subsequently, the prepared hydantoin transporter DNA is inserted into a vector DNA to construct a recombinant DNA, and a cell is transformed with the recombinant DNA vector to construct a transformant. The transformant is then incubated in the culture medium to express the hydantoin transporter DNA.

The DNA to be inserted into the vector DNA may be any DNA as long as introduction of the DNA results in expression of the hydantoin transporter DNA of the present invention.

Examples of the hydantoin transporter genes to be inserted into the vector DNA may include:

(a) a DNA including the base sequence described in SEQ ID No. 1, (b) a DNA which hybridizes under the stringent condition with a DNA including the base sequence which is complementary to the base sequence described in SEQ ID No. 1, and encodes a protein having the hydantoin-transporter activity, (c) a DNA encoding a protein including the amino acid sequence described in SEQ ID No. 2, and (d) a DNA encoding a protein having an amino acid sequence that has substitution, deletion, insertion, or inversion of one or several amino acid residues in the amino acid sequence described in SEQ ID No. 2 and having the hydantoin-transporter activity.

In the transformant of the present invention, it is preferable that the hydantoin transporter is expressed as a membrane protein. However, in the production process, the hydantoin transporter may exist anywhere other than in the biomembrane. That is, there are a variety of possible locations of the transporter depending on the use thereof, such as a soluble protein, an inclusion body of protein formed by protein folding, and so on. In this case, however, the hydantoin transporter has to be solubilized with a solubilizer after the expression of the hydantoin transporter, and the solubilized transporter further has to be reconstituted on the membrane which is an obstacle to hydantoin transportation. The solubilizers may include surfactants such as n-Dodecyl-β-D-maltoside (DDM), n-octyl-β-D-glucoside (OG) and the like.

When the hydantoin transporter DNA of the present invention is expressed using recombinant DNA techniques, host cells to be transformed may include bacteria cells, actinomycetes cells, yeast cells, fungi cells, plant cells, animal cells, insect cells, and the like. Among these, the bacteria cells for which host-vector systems have been developed may include bacteria of the genus *Escherichia*, bacteria of the genus *Pseudomonas*, bacteria of the genus *Corynebacterium*, bacteria of the genus *Bacillus*, and the like. The preferable host is *Escherichia coli*, since there are many reports of producing proteins on a large scale using *Escherichia coli*. A method for producing the transformant using *Escherichia coli* will be explained hereinbelow.

Promoters to be used for expressing the DNA that encodes the hydantoin transporter may include promoters typically used in producing heterogeneous proteins in *Escherichia coli*. Examples thereof may include potent promoters such as T7 promoter, trp promoter, lac promoter, tac promoter, PL promoter, and the like.

In order to increase the production amount, it is preferable to further connect a terminator, i.e. a transcription termination sequence, downstream of the hydantoin transporter gene. The terminator may include the T7 terminator, fd phage terminator, T4 terminator, the terminator of tetracycline-resistant gene, the terminator of *Escherichia coli* trpA gene, and the like.

The vector for introducing the gene encoding hydantoin transporter into *Escherichia coli* may preferably be a multi-copy type. Examples thereof may include a plasmid having a replication origin derived from Col E1, such as pUC plasmid, pBR322 plasmid, and derivatives thereof. "Derivative" herein means a plasmid which is modified by substitution, deletion, insertion, addition or inversion of bases and the like. As used herein, modification may include mutation treatment by mutating agents or UV radiation and the like, or modification by natural mutation and the like. In the present invention, pUC plasmid is preferred, and, pTTQ plasmid (pTTQ18 vector and the like) which is induced from pUC plasmid is especially preferred.

For facilitating selection of the transformants, the vector may preferably have a marker such as an ampicillin-resistant gene and the like. Such a plasmid is commercially available as expression vector having a potent promoter (pUC series (Takara Shuzo Co., Ltd.), pPROK series (Clontech), pKK233-2 (Clontech) and the like).

The recombinant DNA may be obtained by ligating the promoter, the gene encoding the hydantoin transporter, and the terminator in this order to give a DNA fragment, and further inserting the same into the vector DNA.

A host cell may be transformed with the recombinant DNA, and this transformant may be cultivated for producing the hydantoin transporter of the present invention. The transformed host may include strains which are typically used in the expression of heterogeneous genes. *Escherichia coli* BLR strain is especially preferred. A method for conducting transformation and a method for selecting the transformant are described in, e.g., Molecular Cloning, 2nd edition, Cold Spring Harbor press (1989).

The culture medium for cultivating the transformant may include a culture medium which is typically used for cultivating *Escherichia coli*, such as M9-casamino acid medium, LB medium and the like. The conditions for cultivation and induction of the production may be appropriately selected depending on kind of marker of the employed vector, promoter, host microorganism, and the like.

When the DNA described in SEQ ID No. 1 is used as the DNA encoding the transporter, the transporter having the amino acid sequence described in SEQ ID No. 2 is produced.

Cultivation of the present recombinant cell may be performed either by liquid cultivation or solid cultivation. The industrially advantageous method may be an aerated submerged stirring cultivation. Nutrition sources for the nutrition culture medium may include a carbon source, a nitrogen source, an inorganic salt, and other micronutrient sources which are conventionally used in microorganism incubation. Any nutrition source that the employed strain can utilize can be used.

An aerobic condition may be achieved by aeration. Cultivating temperature may be in any range in which the microorganisms grow and the hydantoin transporter is produced. Therefore, the cultivation temperature is not strictly limited, but usually 10 to 50° C., and preferably 30 to 40° C. Cultivation time is varied depending on other cultivation conditions. For example, the cultivation time may be adjusted so that a maximum production of the hydantoin transporter takes place. The cultivation may be performed usually for 5 hours to 7 days, and preferably for 10 hours to 3 days or so.

Furthermore, the transformant of the present invention is preferably a cell which is capable of producing an enzyme that catalyzes the reaction to produce useful compounds from the hydantoin compound, and of accumulating at least a part of the enzyme within the cell. Such a transformant takes up the hydantoin compound into the cell by the hydantoin transporter, and produces the useful compounds from the hydantoin compound by the enzyme in the cell. In other words, the inside of the transformant cell is the location where the substrate encounters the enzyme and the enzymological reaction takes place.

Such a transformant may be constructed by introducing the present hydantoin transporter DNA into a host cell which produces an enzyme catalyzing the reaction for producing useful compounds from the hydantoin compound. Alternatively, a DNA encoding an enzyme catalyzing the reaction for producing useful compounds from the hydantoin compound may be prepared and then introduced into a host cell such as *Escherichia coli*, together with the hydantoin transporter DNA of the present invention, and co-expressed. To ligate the DNA encoding such an enzyme to the gene encoding the transporter for the aforementioned transformation, reading frames of the codons should correspond to each other. This may be done by linking at a suitable restriction enzyme site, or by using synthesized DNA having a suitable sequence.

The enzyme catalyzing the reaction for producing useful compounds from the hydantoin compound is not particularly limited and any known enzyme may be used. Particularly preferable enzymes may include a hydantoinase (HHase). That is, the transformant of the present invention is preferably a cell which produces HHase in addition to the hydantoin transporter of the present invention. Such a transformant effectively uptakes the 5-substituted hydantoin compound from the outside of the cell into the cell, and hydrolyzes the 5-substituted hydantoin compound by HHase which is produced therein by the cell itself to produce N-carbamylamino acid. The produced N-carbamylamino acid may further be hydrolyzed by carbamylase (CHase) and the like, to produce an amino acid. Therefore, the transformant may suitably be used for producing the amino acid from the 5-substituted hydantoin compound.

HHase produced by the transformant may be an optically specific HHase or an optically non-specific HHase. "Optically specific" herein means specificity to either one of the L-isomer or R-isomer. Specifically, it refers to a highly optical selectivity substantially specific to only one isomer as the substrate, and not to the other isomer.

It is known that the optically non-specific HHase exists in, for example, *Microbacterium liquefaciens* AJ3912 (U.S. Pat. No. 7,098,020) which is the source for obtaining the hydantoin transporter of the present invention, and also in *Arthrobacter aurescens* (J. Biotechnol. Vol. 61, page 1, 1998).

On the other hand, the optically specific HHase can specifically produce an optically active N-carbamyl-L-amino acid or N-carbamyl-D-amino acid. In this case, a carbamylase (CHase) may be used subsequently to produce the optically active amino acid. Alternatively, a chemical hydrolysis treatment with nitrous acid may be conducted for producing a high yield of the optically active amino acid while maintaining the optical activity.

For example, it is known that bacteria of the genus *Bacillus* has thermo-resistant D-HHase enzymes which may be used for producing N-carbamyl-D-amino acid. Examples of such an enzyme may include HHase of *Bacillus stearothermophilus* ATCC 31195 (Appl. Microbiol. Biotechnol. Vol. 43, page 270, 1995) and the like.

*Bacillus stearothermophilus* ATCC 31195
(i) Name and address of Depository authority
Name: American Type Culture Collection
Address: P.O. Box 1549, Manassas, Va. 20108, USA, and
(ii) Deposit No.: ATCC 31195

It is known that L-HHase which is specific to the L-isomer of the hydantoin compound exists in, for example, *Bacillus* sp. AJ 12299 (JP-A-1988-24894).

*Bacillus* sp. AJ 12299 strain
(i) Name and address of Depository authority
Name: International Patent Organism Depositary, National Institute of Advanced Industrial Science and Technology
Address: Central 6, 1-1-1 Higashi, Tsukuba, Ibaraki, Japan (Zip code: 305-8566)
(ii) Deposit date: Jul. 5, 1986
(iii) Deposit No.: FERM BP-7646 (formerly FERM P-8837, transferred to International Patent Organism Depositary on Jun. 27, 2001)

If an optically specific HHase is used to hydrolyze the 5-substituted hydantoin compound, an enantiomer which is not a substrate remains unreacted. That is, if D-HHase is used, the L-isomer of the hydantoin compound remains unreacted, and if L-HHase is used, the D-isomer of the hydantoin compound remains unreacted.

To efficiently racemize the non-substrate enantiomer to convert such an enantiomer to the substrate enantiomer in order to achieve effective racemization, the transformant of the present invention may preferably be a cell that additionally produces a 5-substituted hydantoin racemase (HRase). That is, the transformant of the present invention may preferably produce two enzymes that are HHase and HRase, in addition to the hydantoin transporter of the present invention. Expression of the hydantoin transporter, HHase and HRase in a single cell may enable an efficient production of the optically active N-carbamylamino acid with an efficient racemization of the non-substrate enantiomer for converting the same to the substrate enantiomer.

Such HRase exists in, for example, *Microbacterium liquefaciens* AJ3912 (JP-A-2002-330784) which is the source for obtaining the hydantoin transporter of the present invention, and also in *Flavobacterium* sp. AJ11199 (FERM-P4229) (Japanese Patent Appln. Publication No. 2003-210176), *Pasteurella pneumotropica* AJ11221 (FERM-P4348) (Japanese Patent Appln. Publication No. 2003-210177) and the like. *Pasteurella pneumotropica* AJ11221 was originally deposited as *Moraxella nonliquefaciens*, but as a result of re-identification, it was identified as a microorganism belonging to *Pasteurella pneumotropica*.

*Flavobacterium* sp. AJ11199
(i) Name and address of Depository authority
Name: International Patent Organism Depositary, National Institute of Advanced Industrial Science and Technology
Address: Central 6, 1-1-1 Higashi, Tsukuba, Ibaraki, Japan (Zip code: 305-8566)
(ii) Deposit date: May 1, 1981
(iii) Deposit No.: FERM BP-8063 (formerly FERM P-4229, transferred to International Patent Organism Depositary on May 30, 2002)

*Pasteurella pneumotropica* AJ 11221 strain
(i) Name and address of Depository authority
Name: International Patent Organism Depositary, National Institute of Advanced Industrial Science and Technology
Address: Central 6, 1-1-1 Higashi, Tsukuba, Ibaraki, Japan (Zip code: 305-8566)
(ii) Deposit date: May 1, 1981
(iii) Deposit No.: FERM BP-8064 (formerly FERM P-4348, transferred to International Patent Organism Depositary on May 30, 2002)

In order to produce N-carbamylamino acid from the 5-substituted hydantoin compound and subsequently hydrolyze N-carbamylamino acid in the transformant cell for producing the optically active amino acid, it is preferable that the transformant of the present invention additionally produces carbamylase (CHase). That is, the transformant of the present invention may preferably be the cell producing two enzymes of HHase and CHase, or three enzymes of HHase, HRase, and CHase in addition to the hydantoin transporter of the present invention.

The transformant wherein three of the hydantoin transporter, HHase, and CHase, or four of hydantoin transporter, HHase, HRase, and CHase are expressed in a single cell can effectively uptake the 5-substituted hydantoin compound from the outside into the cell, and hydrolyze the 5-substituted hydantoin compound by HHase which is produced therein by the cell itself, to produce N-carbamylamino acid. The N-carbamylamino acid thus produced may subsequently be hydrolyzed in the cell by CHase which is produced by the cell itself, to produce the objective amino acid.

Even if HHase does not have an optically specific hydrolyzing activity, the produced amino acid may become a D- or L- optically active isomer if CHase has an optical specificity. In this case, an unreacted enantiomer of N-carbamylamino acid may remain in the reaction system. That is, if CHase specifically hydrolyzes N-carbamyl-L-amino acid to produce L-amino acid, N-carbamyl-D-amino acid may remain. If CHase produces a D-amino acid, N-carbamyl-L-amino acid may remain in the reaction system. However, in this case, HHase slightly catalyzes a reverse reaction. That is, HHase slightly catalyzes dehydrocondensation of the remaining unreacted enantiomer of the N-carbamylamino acid to produce the 5-substituted hydantoin compound. Therefore, even if HHase does not have optically-specific hydrolysis activity, the optically active amino acid can be produced with a high yield by the combination of the above-described HRase with the hydantoin transporter, Hhase, and optically specific CHase.

It is known that CHase which specifically hydrolyzes the D-isomer of N-carbamylamino acid, exists in, for example, *Agrobacterium* sp. AJ 11220 (JP-B-1981-003034). *Agrobacterium* sp. AJ 11220 was originally deposited as *Pseudomonas* sp. AJ 11220, but as a result of re-identification, it was identified as a microorganism belonging to *Agrobacterium* sp.

*Agrobacterium* sp. AJ 11220 strain (i) Name and address of Depository authority Name: International Patent Organism Depositary, National Institute of Advanced Industrial Science and Technology Address: Central 6, 1-1-1 Higashi, Tsukuba, Ibaraki, Japan (Zip code: 305-8566)

(ii) Deposit date: Dec. 20, 1977

(iii) Deposit No.: FERM BP-7645 (formerly FERM P-4347, transferred to International Patent Organism Depositary on Jun. 27, 2001)

Furthermore, it is known that CHase which specifically hydrolyzes L-isomer of N-carbamylamino acid exists in *Microbacterium liquefaciens* AJ3912 (JP-A-2002-330784) which is the source for obtaining the hydantoin transporter of the present invention, and also in *Bacillus* sp. AJ12299 that has been described above with regard to L-HHase.

In the production of the amino acid from the 5-substituted hydantoin compound using the transformant which produces the present hydantoin transporter with HHase, HRase, CHase and the like, a reaction liquid is prepared so as to contain the 5-substituted hydantoin compound as well as the cultured liquid of the transformant, an isolated cell or a washed cell. The reaction liquid may further contain nutrients which are required for growth of the transformant such as a carbon source, a nitrogen source, an inorganic ion and the like. Addition of organic micronutrients such as vitamins, amino acids and the like may bring about desired results in most of cases. For carrying out the reaction, the reaction liquid may be stirred or left stand at appropriate temperature of 20 to 30° C. and pH of 4 to 10 for 8 hours to 5 days.

The concentration of the 5-substituted hydantoin compound as a substrate may preferably be 1 µM or higher, and more preferably 100 µM or higher. By keeping the substrate concentration at 1 µM or higher, the substrate may effectively be uptaken into the cell of the transformant. The 5-substituted hydantoin compound may be added fractionally, to maintain the substrate concentration in the reaction liquid.

The amino acid produced from the 5-substituted hydantoin compound accumulates in the transformant cells or in the reaction liquid. The produced amino acid may be isolated and purified by any known method.

EXAMPLES

The present invention will be described in more detail with reference to the following non-limiting Examples.

$^3$H-labelled 5-L-benzyl hydantoin ($^3$H-BH, ICN) and $^3$H-labelled 5-L-indolylmethyl hydantoin ($^3$H-IMH, ICN) were used as substrates in the assay for evaluating the uptake of the 5-substituted hydantoin. $^3$H-BH and $^3$H-IMH were each synthesized from $^3$H-L-phenylalanine or $^3$H-L-tryptophane and potassium cyanide. The synthesized $^3$H-BH and $^3$H-IMH were preserved at −20° C. The concentration of the solution was calculated from the absorbance of the solution (BH; $\epsilon_{257nm}$=184/M/cm, IMH; $\epsilon_{280nm}$=5440/M/cm).

Example 1

Preparation of the MHP Recombinant 1.1. Strain and Method for Cultivation

*E. coli* strain BLR was used for the analysis of MHP. The genotype of the *E. coli* strain BLR is presented below (Table 1).

TABLE 1

| Straits | Genotype | Source/Reference |
|---|---|---|
| BLR | F−, ompT, hsdS B($r_B^- m_B^-$), gal, dcm Δ (srl − recA)306::TN10 | Novagen |

1.2. Plasmid

Plasmid pTTQ18 was used to express the transporter. In order to confirm expression of the transporter and to facilitate purification, a plasmid was constructed with an RGSHis6-Tag inserted at the C-terminal end of the transporter according to the method described by Henderson, et al. MHP amplified by PCR was inserted between EcoRI and PstI among the multicloning sites of this plasmid, and the plasmid pSHP11H which expresses a protein containing the RGSHis6-Tag at the C-terminal (MHPH$_6$ (SEQ ID No. 3)) was constructed and used. The *E. coli* strain BLR was transformed with this plasmid to obtain the MHP-expressing strain *E. coli* BLR/pSHP11H.

Figure 2:
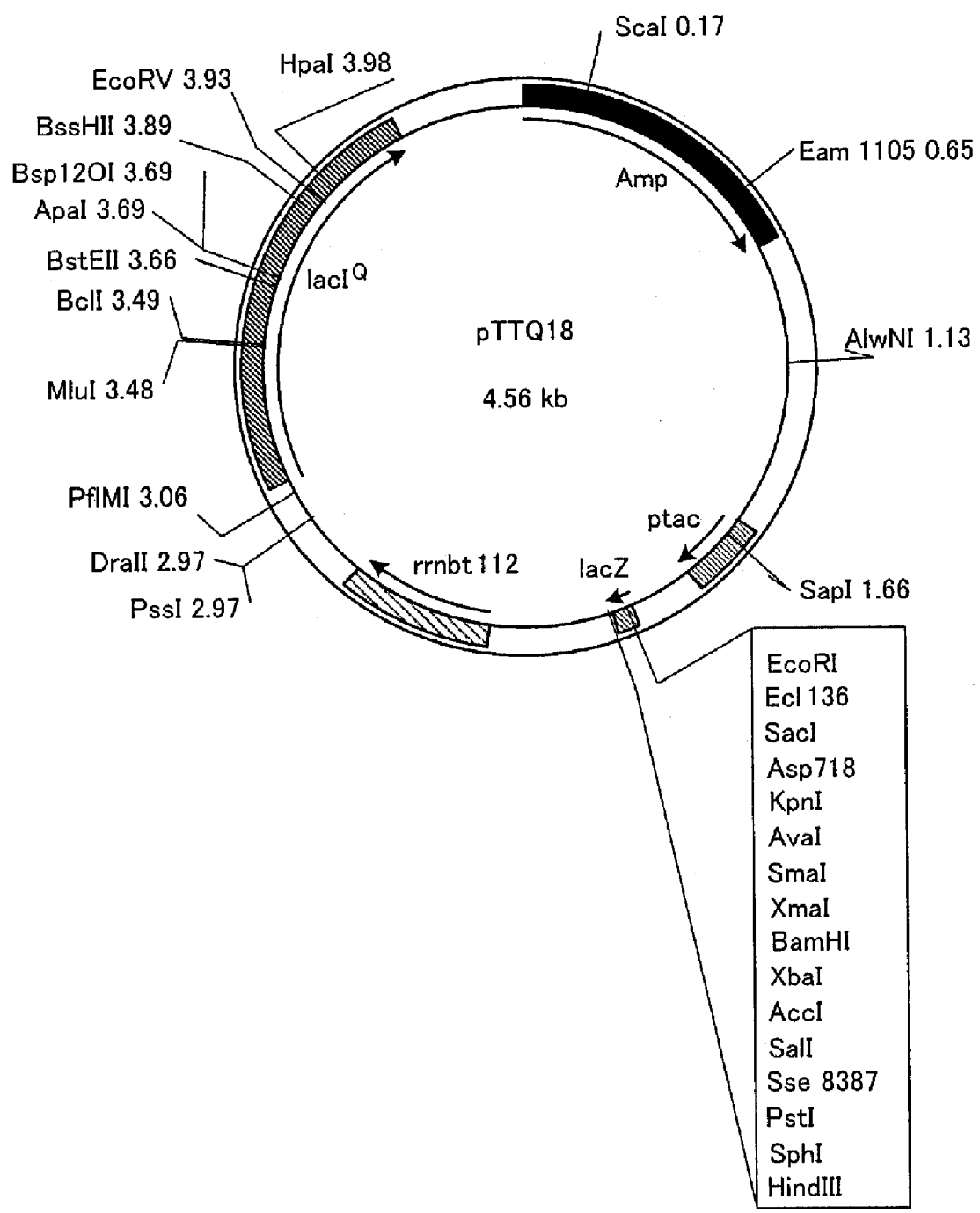
FIG. 2 illustrates the structure of plasmid pTTQ18.

The structure of the expression plasmid pTTQ18 is presented in FIG. 2. A list of the plasmids used in the present study is presented in Table 2. The PCR primers used in the construction of pSHP11H are presented in Table 3 (SEQ ID No. 5, 6) (For pTTQ18, see M. J. R. Stark, Gene 51:255-267, (1987). Multicopy expression vectors carrying the lac repressor gene were used for regulation of high-level expression of genes in *Escherichia coli* (Gene 51: 255-267), and to insert RGSHis6 into pTTQ18 (P. J. Henderson, C. K. Hoyle and A. Ward (2000) Expression, purification and properties of multidrug efflux proteins, Biochem.Soc. Trans. 28: 513-517)).

TABLE 2

| Plasmids | Relevant genes | Reference |
|---|---|---|
| pTTQ18 | — | Stark 1987 |
| pSHP11H | mhp −RGSH6$^+$ | This work |

TABLE 3

| Plasmids | Position | Primer sequences |
|---|---|---|
| pSHP11H | 5' end | CGTCAATGAATTCGACACCCATCGAAGAGGCT |
| pSHP11H | 3' end | TCCTTCTCCTGCAGGGTACTGCTTCTCGGTGGG |

1.3. Medium and Method for Cultivation

Each preserved strain was refreshed by cultivation on Luria Bertani (LB) agar medium (if necessary, containing 0.1 mg/ml carbenicillin) at 37° C. for about 16 hr. Colonies were isolated from the plate and were cultured in accordance with the following method.

*E. coli* BLR/pSHP11H, which was isolated from the refreshed plate, was then seed-cultured in an LB medium containing 0.1 mg/ml carbenicillin. 5 ml of the cultured strain was inoculated into a 2 L conical flask containing 50 ml of M9 minimal medium (6 g/l Na$_2$HPO$_4$, 3 g/l KH$_2$PO$_4$, 1 g/l NH$_4$Cl, 0.5 g/l NaCl, 2 mM MgSO$_4$, 0.2 mM CaCl$_2$) supplemented with 20 mM glycerol and 0.2% (w/v) casamino acid, and this was cultured at 37° C. until the absorbance at 680 nm reached approximately 0.3 to 0.4. Isopropyl-β-D-thiogalactoside (hereinafter, IPTG) was added to the flask at 0.2 mM (the final concentration), and the whole mixture was again cultured at 27° C. on a rotary shaker (200 rpm) for 12 hours. The cells obtained by this method were used in the substrate-uptake assay.

Example 2

Preparation of Membrane Fraction

French pressing was performed in accordance with M. Futai (1978) Experimental systems for the study of active transport in bacteria, in Bacterial Transport (Rosen, B. P., ed.) pp. 7-41, Marcel Dekker Inc., New York.

A French press manufactured by Aminco (American Instrument Company, Illinois, USA) was used. The cultured and collected cells were resuspended in 15 mM Tris-HCl (pH 7.5) and were subjected to the French press at 20,000 psi. Cell debris and undisrupted cells were removed by centrifugation at 5,000 g for 20 minutes. The supernatant was then centrifuged at 150,000 g for 60 minutes, and the whole membrane fraction was recovered by precipitation. If fractionation is required of the inner membrane and outer membrane, the whole membrane fraction was resuspended in 20 mM Tris-HCl (pH 7.5), 0.5 mM EDTA and 10% glycerol (Tris-EDTA buffer), and was subjected to a sucrose density gradient consisting of 30, 35, 40, 45, 50 and 55% (w/w) solutions, and the two fractions were separately recovered by centrifugation at 105,000 g for 16 hours. Both membrane fractions thus obtained were washed by repeating the procedure of suspending in Tris-EDTA buffer and centrifuging at 150,000 g, for 60 minutes three times. The obtained solution was split into suitable amounts of aliquots, subjected to snap-freezing in an ethanol bath and preserved at −70° C. until use.

2.3. Expression of MHPH$_6$

Figure 3:
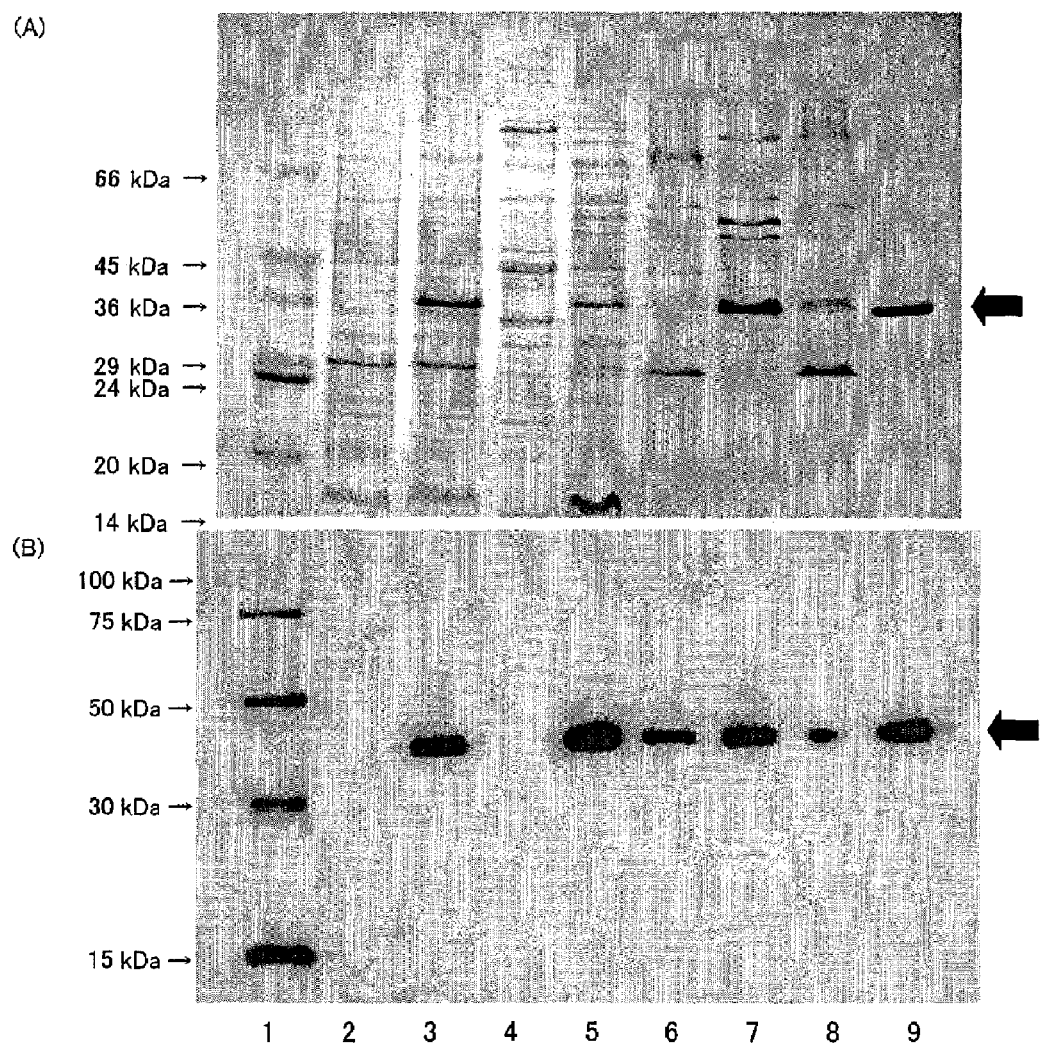
FIG. 3 illustrates the results of (A) SDS-PAGE and (B) Western blotting.

Massive expression of MHPH$_6$ using *E. coli* BLR/pSHP11H was analyzed by SDS-PAGE and Western blotting of the whole membrane fraction prepared by French pressing after cultivation (FIG. 3, lanes 2 and 3).

In the whole membrane fraction of *E. coli* BLR/pSHP11H, expression of a protein estimated to have a molecular weight of 36 kDa, which seems to be MHP, was confirmed in the IPTG-induced sample by SDS-PAGE and Western blotting.

Example 3

Confirmation of MHPH$_6$ Localization, Solubilization and Purification 3.1. Solubilization and Purification of MHPH$_6$ For solubilization of MHPH$_6$, n-dodecyl-β-D-maltoside (DDM) was used as the surfactant, and Ni-NTA Agarose (QIAGEN) was used for purification.

The inner membrane fraction prepared by the French press method was suspended in a solubilizing buffer solution (20 mM Tris-HCl (pH 8.0), 20 mM Imidazole (pH 8.0), 20% (v/v) glycerol, 0.3 M NaCl, 1% (w/v) DDM) to a final protein concentration of 4.6 mg/ml. The solution was moderately stirred on ice for 60 minutes and then centrifuged at 160,000 g for 30 minutes. The supernatant obtained by this centrifugation was taken as the solubilized fraction. The precipitate was suspended in an equal volume of buffer solution as the supernatant, to obtain the non-solubilized fraction. The solubilized fraction thus obtained was added to Ni-NTA agarose (QIAGEN) which was previously equilibrated with a buffer solution for washing (20 mM Tris-HCl (pH 8.0), 20 mM Imidazole (pH 8.0), 10% (v/v) glycerol, 0.05% (w/v) DDM), and the system was left to stand at 4° C. for 3 hours. Then, the supernatant (non-binding fraction) and the resin were separated by centrifugation. The obtained protein-bound resin was washed with the buffer solution for washing, and then filled onto a column. Then, the protein bound to the resin was eluted with an eluent buffer solution (0.2 M Imidazole (pH 8.0), 20% (v/v) glycerol, 0.05% (w/v) DDM).

3.2. Protein Assay

The method of Schaffner and Weissman was employed (W. Schaffner and C. Weissman (1973) A rapid, sensitive, and specific method for the determination of protein in dilute solution, Anal. Biochem. 56: 502-514.). BSA was used as the concentration standard.

3.3. SDS-PAGE

The method of Laemmli was employed for SDS-PAGE (U. K. Laemmli (1970), Cleavage of structural proteins during the assembly of the head of bacteriophage T4, Nature 227: 680-685.), and Coomasie Brilliant Blue R was used to visualize the proteins after electrophoresis. As the molecular weight markers, BSA (66 kDa), Ovalbumin (45 kDa), Glyceraldehyde-3-phosphate dehydrogenase (36 kDa), Carbonic anhydrase (29 kDa), Tripsinogen (24 kDa), Trypsin Inhibitor (20 kDa), and α-Lactalbumin (14.2 kDa) were used (Sigma).

3.4. Western Blotting

The semi-drying mode was employed for protein blotting, and PVDF membranes were used as transfer membranes. In the detection of the RGSH$_6$-tagged proteins, mouse anti-RGSH4 (QIAGEN) was used as the primary antibody, and goat anti-mouse IgG (BIO-RAD) as the secondary antibody. Chemiluminescence was adopted for visualization. 6×His Protein Ladder (MW 100, 75, 50, 30, 15 kDa, QIAGEN) was used as the molecular weight marker for Western blotting.

3.5. Confirmation of MHPH$_6$ Localization, Solubilization and Purification

SDS-PAGE and Western blotting were performed on the fractions prepared by French pressing, as well as the fractions obtained by solubilization with DDM and purification with the nickel-NTA column (FIGS. 3(A) and 3(B)).

From the results of *E. coli* BLR/pSHP11H, the whole membrane fraction of the IPTG-induced sample, and the cytosol fraction, it was confirmed that localization of MHPH$_6$ in the solubilized fraction did not occur, and that MHPH$_6$ expression was localized in the membrane fraction (lane 3 and lane 4 in FIGS. 3(A) and 3(B)). Furthermore, when the whole membrane fraction was separated into the inner and outer membrane fractions, MHPH$_6$ was predominant in the inner membrane fraction (lane 5 and lane 6 in FIGS. 3(A) and 3(B)).

As to the sample solubilized with 1% DDM, it was confirmed that the majority of MHPH$_6$ was solubilized (lane 7 and lane 8 in FIGS. 3(A) and 3(B)).

MHPH$_6$ was purified to an electrophoretically single band by a nickel-NTA column, and was estimated to have a molecular weight of 36 kDa by SDS-PAGE (lane 9 in FIGS. 3(A) and 3(B)).

Example 4

Analysis of the N-Terminal Amino Acid Sequence of MHPH$_6$

5 µg of purified MHPH$_6$ was subjected to SDS-PAGE and blotting on a PVDF membrane. The resulting band was visualized by Sulforodamine dyeing and was cut out and analyzed with a Protein Sequencer. The identified sequence was MNSTPIEEAR (SEQ ID No. 7), which is consistent with the N-terminal amino acid sequence of MHP (MST-TPIEEAR), [residues 1-10 of SEQ ID No. 2]) and the N-terminal amino acid sequence of MHPH$_6$ expected from the base sequence substitution (At the 5'-end of ORF, ATGTCGACGACA [residues 1-12 of SEQ ID No. 1] . . . to ATGAATTCGACA . . . [residues 1-12 of SEQ ID No. 3]) during the construction of the expressing vector.

The molecular weight of the expressed MHPH$_6$ on SDS-PAGE was 36 kDa (FIG. 3A), and this value was significantly different from the molecular weight of 54.6 kDa calculated from the sequence. However, from the analysis of the N-terminal amino acid sequence of the purified MHPH$_6$, and from Western blotting using an anti-RGSH$_6$ antibody confirming that the expressed protein retains the RGSH$_6$-tag at the C-terminal (FIG. 3B), it was deduced that the expressed MHPH$_6$ maintained the entire length of the amino acid sequence described in SEQ ID No. 4. This difference in the observed molecular weight was thought to have occurred because the strong hydrophobicity of MHPH$_6$ does not allow complete denaturing even when subjected to the conditions of SDS-PAGE, and the protein maintains a higher order structure to a certain extent.

Example 5

Analysis of the CD Spectrum of MHPH$_6$ and Heat Stability 5.1. Circular Dichroism (CD) Spectroscopy The buffer solution suspending the purified MHPH$_6$ was replaced by 10 mM sodium phosphate (pH 7.6) with 0.05% (w/v) DDM, using an ultrafiltration apparatus (Centricon C50, Millipore). In this buffer solution, the protein concentration was adjusted to 50 µg/ml, and the CD spectroscopy was carried out at 10° C. (JASCO J-715 Spectropolarimeter). The measurement was performed at a wavelength ranging from 190 to 260 nm, and the average value of twenty measurements was taken. Furthermore, the change in the secondary structure of MHPH$_6$ (heat stability) was observed by measuring the change of the CD unit value at a wavelength of 222 nm as the temperature of the sample was varied from 10° C.—>90° C.—>10° C. (the temperature change was made 10° C. at a time, and the length of time at each temperature was approximately 10 minutes).

5.2. Analysis of the CD Spectrum of MHPH$_6$ and Temperature Stability

Figure 4A:
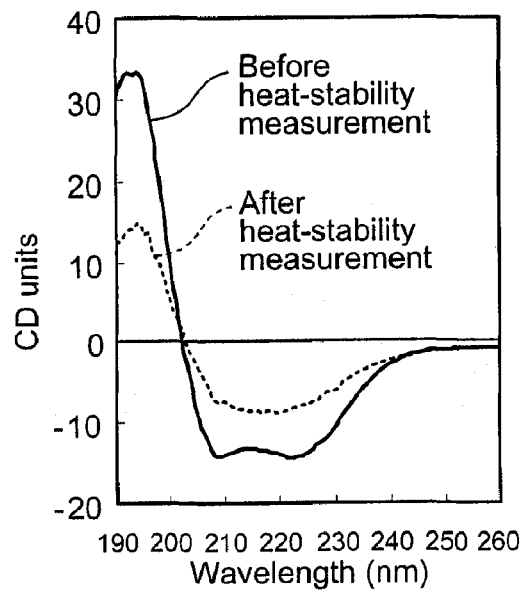
FIG. 4A illustrates the CD spectrum of $MHPH_6$.
Figure 4B:
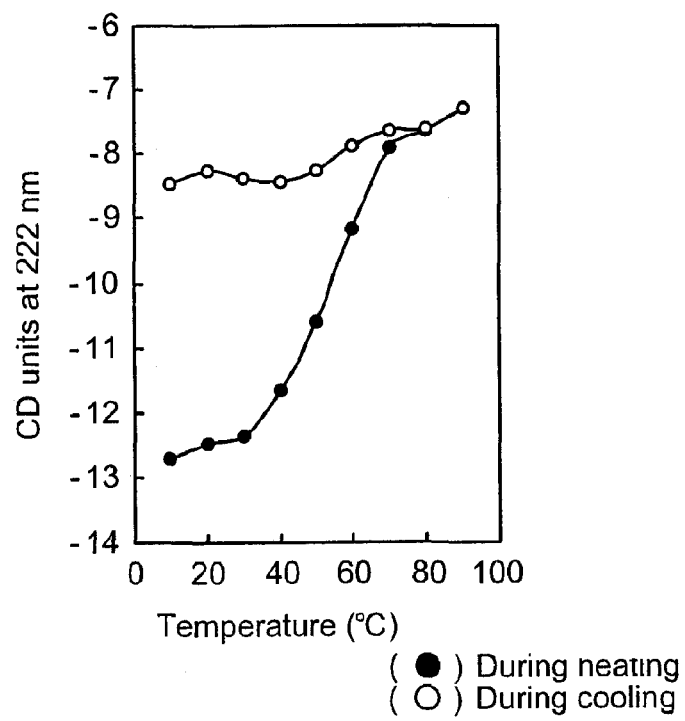
FIG. 4B illustrates the temperature stability of $MHPH_6$.

As a result of the CD spectrum analysis of the purified MHPH$_6$, it was determined that MHPH$_6$ maintained the higher order structure even after solubilization and purification (FIG. 4A). Furthermore, from the measurement of heat stability, it was observed that the higher structure of MHPH$_6$ began to be destroyed at 30° C. or higher and was almost completely destroyed at 70° C. (FIG. 4B). The thermal denaturation was irreversible. After the elevation of temperature up to 90° C., the destroyed higher structure of MHPH$_6$ was not recoverable even if the temperature of the sample was lowered again (FIGS. 4A and 4B).

Example 6

Uptake Assay Using Intact Cells 6.1. Method for Assay

The methods of West (I. C. West (1970), Lactose transport coupled to proton movements in *Escherichia coli*. Biochem. Biophys. Res. Commun. 41: 655-661.) and Henderson (P. J. F. Henderson and A. J. S. Macpherson (1986), Assay, genetics, proteins, and reconstitution of proton-linked galactose, arabinose, and xylose transport systems of *Escherichia coli*, Methods Enzymol. 125: 387-429.) were employed.

The collected cells were washed three times with 150 mM KCl, 5 mM MES (2-[N-Morpholino]ethanesulphonic acid) (pH 6.6) and were then used in the assay. The basic reaction conditions included uptake initiation by adding glycerol to a final concentration of 20 mM to a cell suspension having an absorbance at about $A_{680}$ of approximately 2 to 4, followed by aeration at 25° C. for 3 minutes, and then addition of an RI-labelled substrate (relative RI activity: $^3$H-BH 107 Bq/nmol, $^3$H-IMH 241 Bq/nmol) to a final concentration of 25 µM. After the onset of the reaction (aeration was continued), sampling was done over time. Immediately after the sampling, each aliquot was passed through a filter with a pore size of 0.45 µm (pre-incubated in a washing solution of 150 mM KCl and 5 mM MES (pH 6.6)) which was then washed sufficiently with a washing solution. The radiation remaining on the filter was measured by a liquid scintillation counter. The uptake activity was expressed in terms of the dry cell weight that was calculated by taking the absorbance $A_{680}=1$ as the dry cell concentration of 0.68 mg/ml (Ashworth and Kornberg, Biological Sciences, 165(999): 179-188, (1966)). Furthermore, the initial uptake rate was calculated based on the data obtained at 15 seconds after the addition of substrate, and expressed in terms of the uptake amount per minute.

In the measurement of the inhibitory activity of the inhibitor, the inhibitor was added at the time of onset of aeration. That is, it was pre-incubated with the cells for 3 minutes prior to the substrate addition. The inhibitor used was 2,4-dinitrophenol (DNP), and the final concentration during the reaction was 20 mM.

For varying the pH of the reaction liquid, 10 mM potassium acetate (pH 4.0), 5 mM MES (pH 4.9, 6.1, 6.6, 7.1, 7.9), 10 mM Tris-HCl (pH 8.0) and 10 mM glycin-NaOH (pH 10.0) were used when appropriate.

6.2. Uptake of the 5-Substituted Hydantoin by Intact Cells of *E. coli* BLR/pSHP11H The ability of the intact cells of *E. coli* BLR/pSHP11H to uptake L-BH (open triangle, solid triangle) or L-IMH (open circle, solid circle) was measured.

In strain *E. coli* BLR/pSHP11H, induced samples (solid circle, solid triangle) resulted in higher uptake ability than the uninduced samples (open circle, open triangle) when either L-BH or L-IMH was used as the substrate (FIG. 5). For either of the substrates, the uptake amount continued to increase up to 5 minutes after the addition of the substrate, and reached 0.27 nmol/mg (L-BH) and 0.91 nmol/mg (L-IMH). The initial uptake rates were 0.64 nmol/mg/min (L-BH) and 2.5 nmol/mg/min (L-IMH). In comparing the two substrates, the uptake amount 5 minutes after the addition of substrate was 3.4 times greater with L-IMH than with L-BH, and the initial uptake rate was 3.9 times faster with L-IMH as the substrate.

Figure 6:
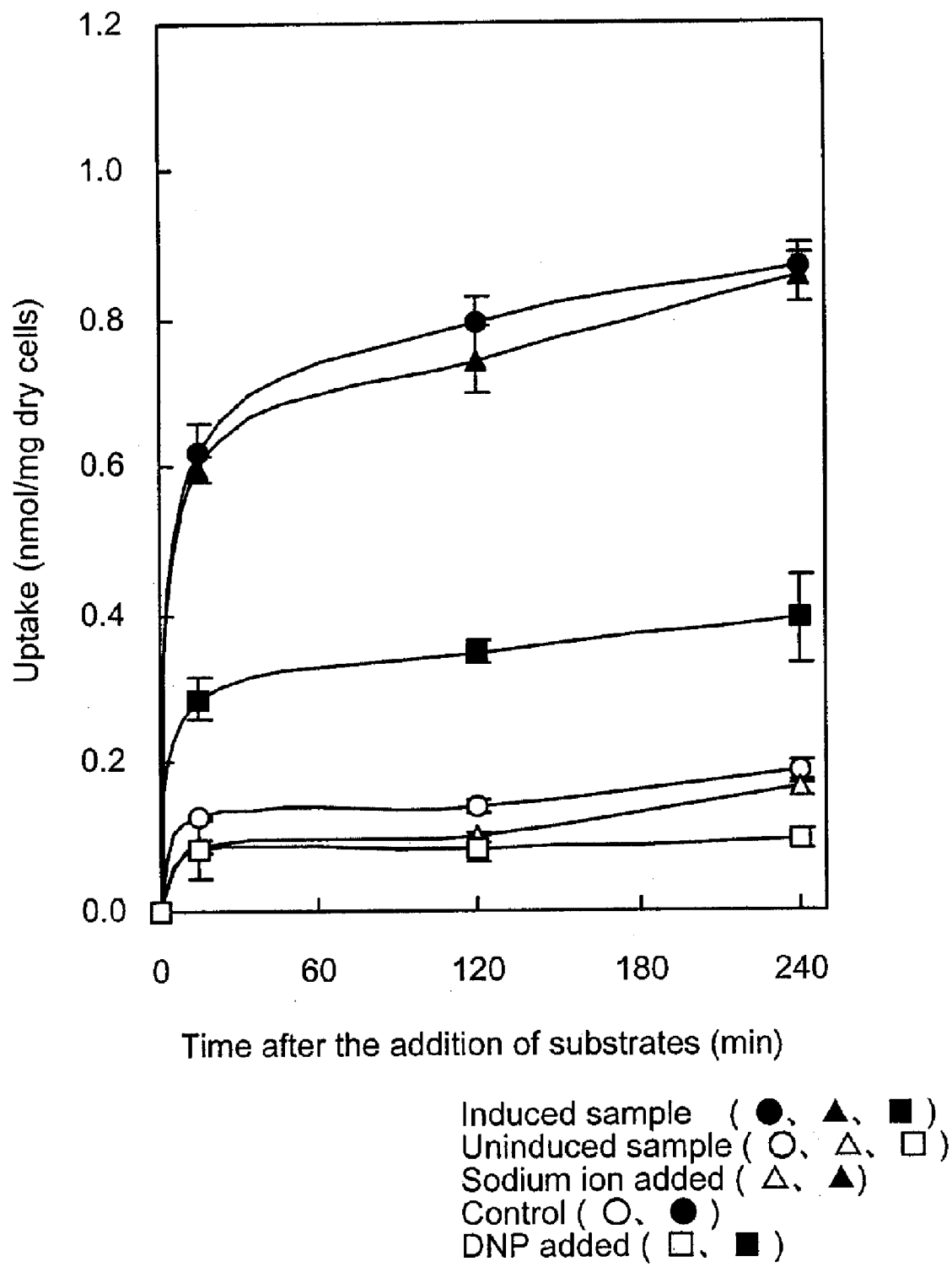
FIG. 6 illustrates the effect of sodium and DNP on L-IMH uptake by *E. coli* BLR/pSHP11H.

6.3. The Effect of Sodium Ions and DNP on the L-IMH Uptake by E. coli BLR/pSHP11H The effect of sodium ions and DNP on the L-IMH uptake by E. coli BLR/pSHP11H were measured (FIG. 6).

Although 10 mM of sodium ions were added to the reaction liquid of L-IMH uptake assay, the ions did not affect the L-IMH uptake in either the induced sample (solid triangle) or uninduced sample (open triangle). When DNP was added, it had substantially no effect on the L-IMH uptake in the uninduced sample (open square), but it decreased the amount of L-IMH uptake in the induced sample (solid square).

6.5. pH-Dependency of L-IMH Uptake by Strain E. coli BLR/pSHP11H

Figure 7:
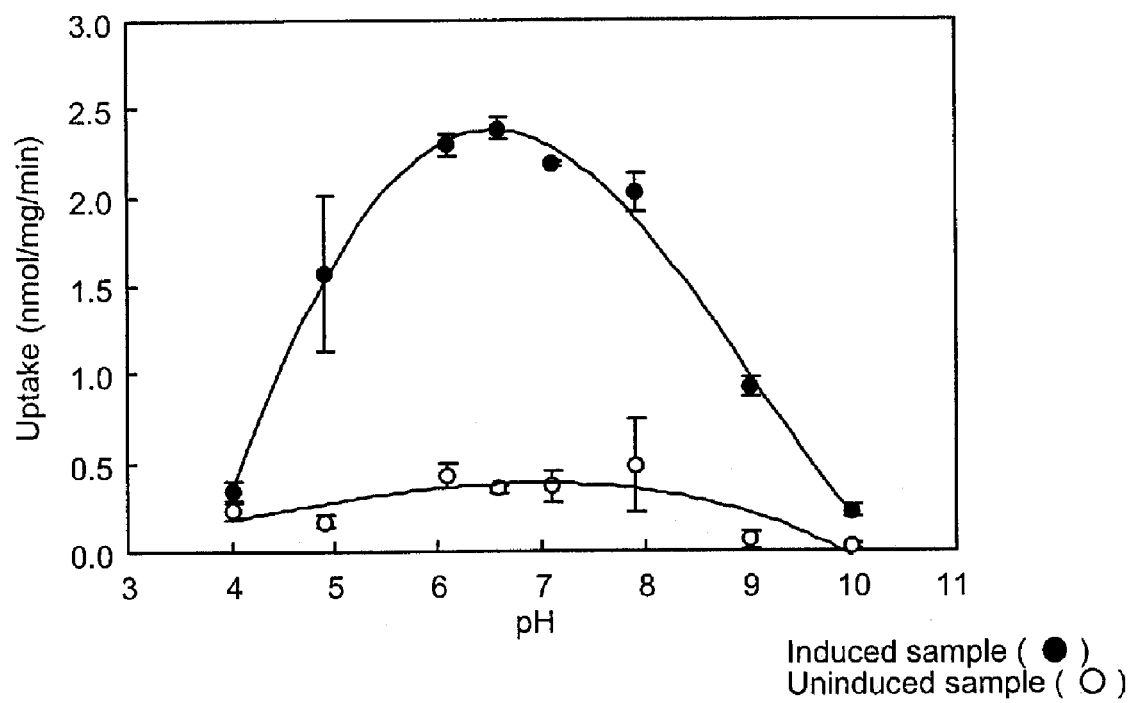
FIG. 7 illustrates the pH-dependency of L-IMH uptake by *E. coli* BLR/pSHP11H.

The pH of the reaction solution for L-IMH uptake by E. coli BLR/pSHP11H was varied between pH 4.0 and 10.0, and the initial rate of L-IMH uptake at each pH was measured (FIG. 7). As a result, the initial uptake rate was maximal at pH 6.6 in both the induced sample (solid circle) and uninduced sample (open circle), and the optimum pH range for the uptake reaction for L-IMH was in the neutral region (pH 6 to 8). As the pH deviated away from neutral, either to the acidic or to the alkaline, the initial uptake rate decreased, and the initial uptake rate at pH 4.0 or pH 10.0 both decreased to approximately 10% as compared with the initial rate at pH 6.6.

Example 7

Screening of the Substrate for MHP 7.1. Method for Screening

25 μM of $^3$H-L-BH was employed as the RI-labeled substrate in the above-described reaction using intact cells, and a reaction liquid was prepared by adding 250 μM of a candidate substrate (cold). The uptake amount of $^3$H-L-BH after 3 minutes from the addition thereof was compared with the amount without the candidate substrate, to calculate the competitive inhibitory activity of each candidate substrate against L-BH, for evaluating the potentiality of each candidate substance as the substrate for MHP.

7.2. Screening for the Substrate of $MHPH_6$

Figure 8:
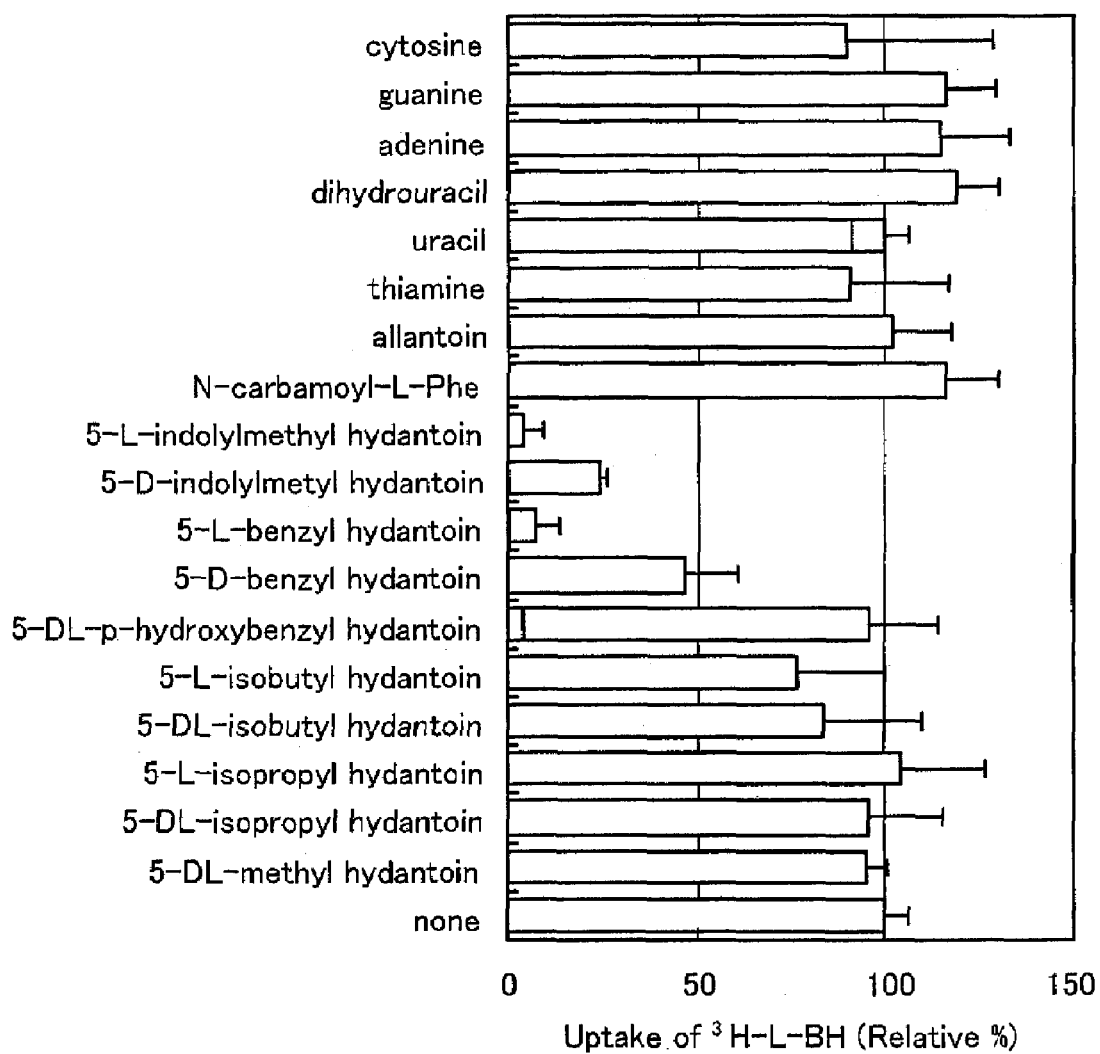
FIG. 8 illustrates the results of the screening of substrates for $MHPH_6$.

Affinity of a variety of compounds to $MHPH_6$ was measured based on the competitive inhibitory activity thereof against L-BH uptake by E. coli BLR/pSHP11H, to search for substrates for $MHPH_6$ (FIG. 8). Among 18 candidate compounds including cold L-BH, strong activity of competitive inhibition was shown by the following four compounds: L-BH, D-BH, L-IMH, and D-IMH. Weaker inhibitory activity was indicated by the addition of 5-substituted hydantoin compounds such as 5-DL-methyl hydantoin, 5-DL-isopropyl hydantoin, 5-L-isopropyl hydantoin, 5-DL-isobutyl hydantoin, 5-L-isobutyl hydantoin, 5-DL-p-hydroxybenzyl hydantoin, which suggest the potential activity of $MHPH_6$ for transporting many 5-substituted hydantoin compounds. These results suggest that $MHPH_6$ has a particularly strong activity for transporting 5-substituted hydantoin compounds which include aromatic amino acids. These results also suggest that $MHPH_6$ tends to have a strong activity for transporting 5-substituted hydantoin compounds which include hydrophobic amino acids. When the four compounds showing strong inhibitive activity were added, the uptake activities of $^3$H-L-BH (the relative activity with respect to when not adding any compound as 100%) were 7% (L-BH, theoretical value 9%), 47% (D-BH), 3% (L-IMH) and 24% (D-IMH). Measurement with L-IMH resulted in the highest inhibitory activity.

Meanwhile, the addition of allantoin did not result in any inhibition against the uptake of L-BH by $MHPH_6$. Therefore, it was demonstrated that $MHPH_6$ does not have any allantoin transport activity, which implied that $MHPH_6$ was a novel transporter having a different nature from known allantoin transporters.

7.3. Optical Specificity of $MHPH_6$ for Substrate Recognition

Figure 9:
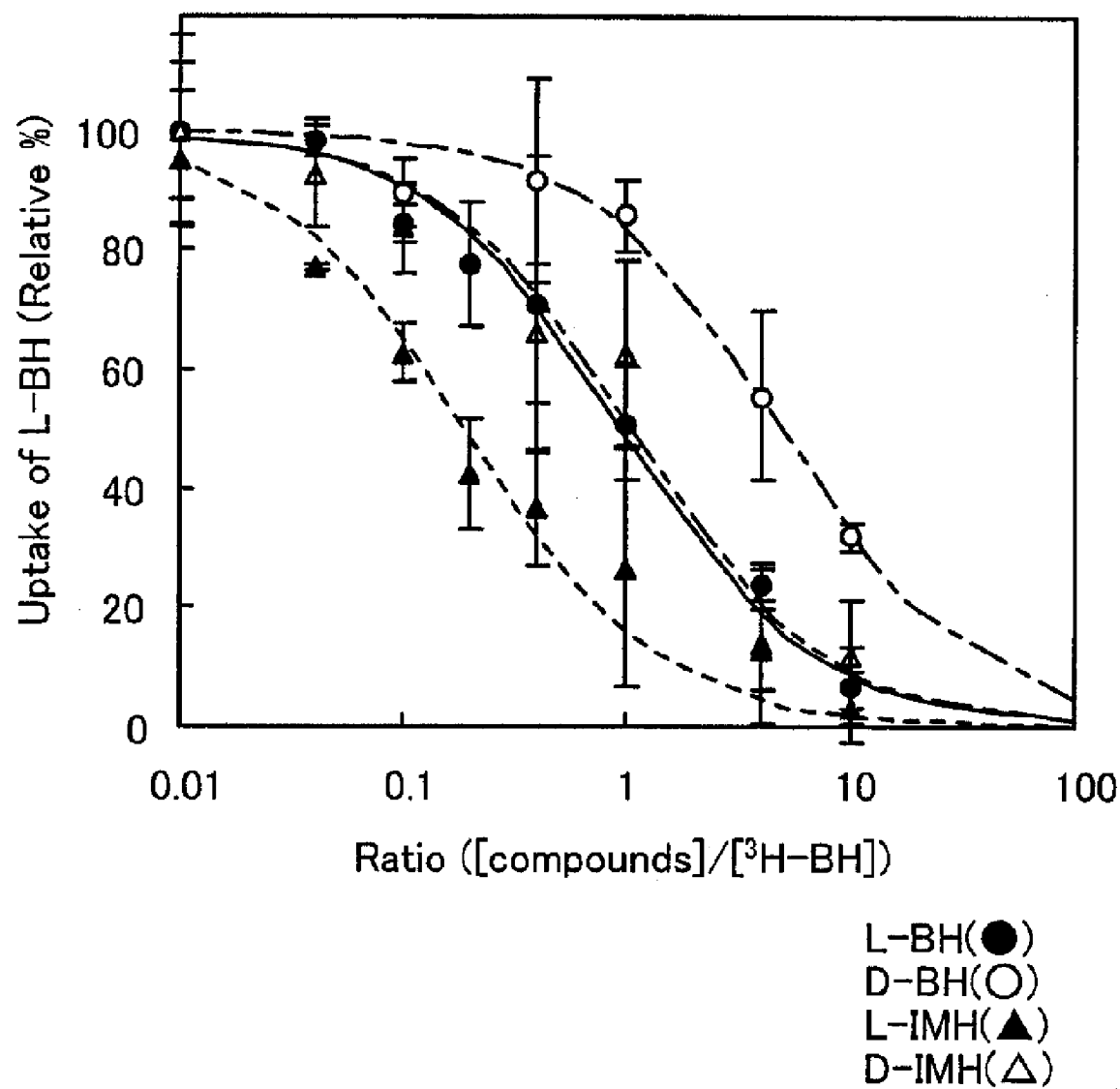
FIG. 9 illustrates the results of the optical specificity of $MHPH_6$ for substrate recognition.

From the results of substrate screening for competitive inhibition against $^3$H-L-BH uptake activity, D- and L-isomers of BH and IMH were selected as candidate substances for the substrate of $MHPH_6$. Therefore, the optical specificity of $MHPH_6$ for these substrates were further investigated (FIG. 9).

The competitive inhibition experiments were carried out, as for substrate screening, with a variety of substrate concentrations. As a result, the affinity of D- and L-BH and D- and L-IMH for $MHPH_6$ was different from one another, and the intensity of the affinity was in the order of L-IMH (solid triangle), L-BH (solid circle), D-IMH (open triangle) and D-BH (open circle) from the strongest. Assuming that $^3$H-L-BH and the added cold compound were under simple competitive inhibition, the experimental results were curve-fitted. As a result, the relative affinity for each compound was calculated to be 5.32 (L-IMH), 1.05 (L-BH, experimental value), 0.96 (D-IMH), and 0.20 (D-BH), with respect to the affinity of L-BH and $MHPH_6$ being 1. L-IMH exhibited the highest affinity which was estimated to be approximately 5 times greater than that of L-BH.

INDUSTRIAL APPLICABILITY

The hydantoin transporter of the present invention is a novel transporter for transporting hydantoin compounds. When present in biomembranes, it mediates the passage of the hydantoin compounds through the membranes. Thus, it becomes possible to produce a transformant having an excellent ability of cellular uptake of the hydantoin compounds, by expressing the hydantoin transporter of the present invention using gene recombination techniques.

Conventionally, in order to extract the enzymes produced by microorganisms, it was necessary to solubilize the enzymes by disrupting the cells before carrying out reactions. However, the hydantoin transporter of the present invention enables an efficient uptake of the hydantoin compounds as substrates into the cells, and thus enables an efficient enzymatic reaction within the cells. Accordingly, the disruption treatment process of the cells, which was necessary in the conventional method to extract the enzyme from the inside of cells, is no longer necessary.

The hydantoin transporter of the present invention may suitably be used in the bioconversion process using intact cells, for performing enzymatic reactions of hydantoin compounds as substrates.

REFERENCES

1. A. Wiese, C. syldatk, R. Mattes and J. Altenbuchner (2001). Organization of genes responsible for the stereospecific conversion of hydantoins to α-amino acids in *Arthrobacter aurescens* DSM3747. Arch. Microbiol. 176: 187-196.

2. K. Watabe, T. Ishikawa, Y. Mukohara and H Nakamura (1992). Cloning and sequencing of the genes involved in the conversion of 5-substituted hydantoins to the corresponding L-amino acid from the native plasmid of *Pseudomonas* sp. NS671. J. Bacteriol. 174: 962-969.

3. B. Wilms, A Wiese, C. Syldatk, R. Mattes (2001). Development of an *Escherichia coli* whole cell biocatalyst for the production of L-amino acids. J. Biotechnol. 86: 19-30.

4. R. Sumrada and T. G. Cooper (1977). Allantoin transport in *Saccharomyces cerevisiae*. J. Bacteriol. 131: 839-847.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. An isolated protein having hydantoin-transporter activity, wherein the amino acid sequence of the protein is selected from the group consisting of:
   (A) an amino acid sequence comprising the sequence SEQ ID No. 2, and
   (B) an amino acid sequence comprising the sequence SEQ ID No. 2, wherein 1 to 10 amino acids are substituted, deleted, inserted, added and/or inverted in the amino acid sequence SEQ ID No. 2.

2. The protein as described in claim 1, wherein said hydantoin-transporter activity comprises transporting a 5-substituted hydantoin compound represented by the following formula (1):

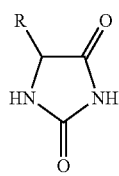

(1)

wherein R is selected from the group consisting of a $C_{1-8}$ straight or branched alkyl group, a $C_{2-8}$ straight or branched alkylene group, an aryl group or aralkyl group having 20 or less carbon atoms, a $C_{1-8}$ mercaptoalkyl group, and a $C_{2-8}$ alkylthioalkyl group.

3. The protein as described in claim 2, wherein R is an aralkyl group having 20 or less carbon atoms.

4. The protein as described in claim 3, wherein R is an indolylmethyl group or a benzyl group.

5. The protein as described in claim 1, wherein the protein is from a microorganism belonging to the genus *Microbacterium*.

6. The protein as described in claim 5, wherein the protein is from *Microbacterium liquefaciens*.

7. The protein as described in claim 6, wherein the protein is from *Microbacterium liquefaciens* AJ3912.

8. The protein as described in claim 1, wherein the protein transports a hydantoin compound selected from the group consisting of 5-indolylmethyl hydantoin, 5-benzyl hydantoin, and combinations thereof.

9. The protein as described in claim 1, wherein said hydantoin-transporter activity is selective for the L-isomer of a 5-substituted hydantoin compound.

10. An isolated protein having hydantoin-transporter activity, wherein the amino acid sequence of the protein comprises sequence SEQ ID No. 2.

11. The protein as described in claim 10, wherein said hydantoin-transporter activity is for transporting a 5-substituted hydantoin compound represented by the following formula (1):

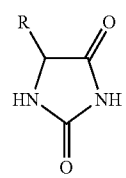

(1)

wherein R is selected from the group consisting of a $C_{1-8}$ straight or branched alkyl group, a $C_{2-8}$ straight or branched alkylene group, an aryl group or aralkyl group having 20 or less carbon atoms, a $C_{1-8}$ mercaptoalkyl group, and a $C_{2-8}$ alkylthioalkyl group.

12. The protein as described in claim 11, wherein R is an aralkyl group having 20 or less carbon atoms.

13. The protein as described in claim 11, wherein R is an indolylmethyl group or a benzyl group.

14. The protein as described in claim 10, wherein the protein is from a microorganism belonging to the genus *Microbacterium*.

15. The protein as described in claim 14, wherein the protein is from *Microbacterium liquefaciens*.

16. The protein as described in claim 15, wherein the protein is from *Microbacterium liquefaciens* AJ3912.

17. The protein as described in claim 10, wherein the protein transports a hydantoin compound selected from the group consisting of 5-indolylmethyl hydantoin, 5-benzyl hydantoin, and combinations thereof.

18. The protein as described in claim 10, wherein said hydantoin-transporter activity is selective for the L-isomer of a 5-substituted hydantoin compound.

* * * * *

SEQUENCE LISTING

```
<160> NUMBER OF SEQ ID NOS: 7

<210> SEQ ID NO 1
<211> LENGTH: 1470
<212> TYPE: DNA
<213> ORGANISM: microbacterium liquefaciens AJ3912
<220> FEATURE:
<221> NAME/KEY: Inventor: Shun'ichi, Suzuki; Kenzo, Yokozeki; Peter J.F.
      Henderson
<220> FEATURE:
<221> NAME/KEY: CDS
<222> LOCATION: (1)..(1470)
<223> OTHER INFORMATION: hydantoin permease

<400> SEQUENCE: 1 atg tcg acg aca ccc atc gaa gag gct cgc agc ctc ctg aac cca tcc      48
Met Ser Thr Thr Pro Ile Glu Glu Ala Arg Ser Leu Leu Asn Pro Ser
1               5                   10                  15 aat gca ccc act cga tac gcc gag cgc tcc gtc ggc ccg ttc tcc ctc      96
Asn Ala Pro Thr Arg Tyr Ala Glu Arg Ser Val Gly Pro Phe Ser Leu
                20                  25                  30 gcg gcc atc tgg ttc gcc atg gcg atc cag gtc gcg atc ttc atc gcc     144
Ala Ala Ile Trp Phe Ala Met Ala Ile Gln Val Ala Ile Phe Ile Ala
            35                  40                  45 gcg gga cag atg acg agc agc ttc cag gtc tgg cag gtg atc gtc gcc     192
Ala Gly Gln Met Thr Ser Ser Phe Gln Val Trp Gln Val Ile Val Ala
        50                  55                  60 atc gcc gca ggc tgc acg atc gca gtg atc ctc ctc ttc ttc acc cag     240
Ile Ala Ala Gly Cys Thr Ile Ala Val Ile Leu Leu Phe Phe Thr Gln
65                  70                  75                  80 agc gcg gcg atc cgc tgg ggc atc aac ttc acg gtc gcc gcg cgg atg     288
Ser Ala Ala Ile Arg Trp Gly Ile Asn Phe Thr Val Ala Ala Arg Met
                85                  90                  95 cct ttc ggc atc cgc gga tcg ctg atc ccg atc acc ctc aag gcc ctg     336
Pro Phe Gly Ile Arg Gly Ser Leu Ile Pro Ile Thr Leu Lys Ala Leu
                100                 105                 110 ctc tcg ctg ttc tgg ttc ggc ttc cag acg tgg ctg ggc gcg ctg gcg     384
Leu Ser Leu Phe Trp Phe Gly Phe Gln Thr Trp Leu Gly Ala Leu Ala
            115                 120                 125 ctc gat gag atc acg cgt ctc ctc acc gga ttc acg aac ctg ccg ctg     432
Leu Asp Glu Ile Thr Arg Leu Leu Thr Gly Phe Thr Asn Leu Pro Leu
        130                 135                 140 tgg atc gtc atc ttc ggc gcg atc cag gtc gtg acg acc ttc tac ggg     480
Trp Ile Val Ile Phe Gly Ala Ile Gln Val Val Thr Thr Phe Tyr Gly
145                 150                 155                 160 atc acg ttc atc cgc tgg atg aac gtc ttc gcc tcg ccg gtg ctc ctc     528
Ile Thr Phe Ile Arg Trp Met Asn Val Phe Ala Ser Pro Val Leu Leu
                165                 170                 175 gcg atg ggc gtg tac atg gtg tac ctg atg ctc gac ggc gcc gac gtg     576
Ala Met Gly Val Tyr Met Val Tyr Leu Met Leu Asp Gly Ala Asp Val
            180                 185                 190 agc ctc ggc gag gtc atg tcg atg ggt ggc gag aac cct ggc atg ccg     624
```

|     |     |     |     |     |     |     |     |     |     |     |     |     |     |      |
| --- | --- | --- | --- | --- | --- | --- | --- | --- | --- | --- | --- | --- | --- | ---: |
| Ser | Leu | Gly | Glu | Val | Met | Ser | Met | Gly | Gly | Glu | Asn | Pro | Gly | Met | Pro |
|     |     | 195 |     |     |     | 200 |     |     |     |     | 205 |     |     |     |      |
| ttc | tcg | acc | gcg | atc | atg | atc | ttc | gtc | ggc | ggc | tgg | atc | gcg | gtc | gtg | 672 |
| Phe | Ser | Thr | Ala | Ile | Met | Ile | Phe | Val | Gly | Gly | Trp | Ile | Ala | Val | Val |
|     | 210 |     |     |     |     | 215 |     |     |     |     | 220 |     |     |     |      |
| gtg | agc | atc | cac | gac | atc | gtg | aag | gag | tgc | aag | gtc | gac | ccg | aac | gcg | 720 |
| Val | Ser | Ile | His | Asp | Ile | Val | Lys | Glu | Cys | Lys | Val | Asp | Pro | Asn | Ala |
| 225 |     |     |     |     | 230 |     |     |     |     | 235 |     |     |     |     | 240 |
| tcg | cga | gaa | ggt | cag | acg | aag | gcc | gac | gcg | cga | tac | gcc | acg | gcg | cag | 768 |
| Ser | Arg | Glu | Gly | Gln | Thr | Lys | Ala | Asp | Ala | Arg | Tyr | Ala | Thr | Ala | Gln |
|     |     |     |     | 245 |     |     |     |     | 250 |     |     |     |     | 255 |      |
| tgg | ctc | ggc | atg | gtg | ccg | gca | tcc | atc | atc | ttc | gga | ttc | atc | ggc | gcc | 816 |
| Trp | Leu | Gly | Met | Val | Pro | Ala | Ser | Ile | Ile | Phe | Gly | Phe | Ile | Gly | Ala |
|     |     |     | 260 |     |     |     |     | 265 |     |     |     |     | 270 |     |      |
| gcc | tcg | atg | gtg | ctg | gtg | ggg | gag | tgg | aac | ccg | gtc | atc | gcc | atc | acc | 864 |
| Ala | Ser | Met | Val | Leu | Val | Gly | Glu | Trp | Asn | Pro | Val | Ile | Ala | Ile | Thr |
|     |     | 275 |     |     |     |     | 280 |     |     |     |     | 285 |     |     |      |
| gag | gtg | gtc | ggc | ggc | gtg | tcg | atc | ccg | atg | gcg | atc | ctc | ttc | cag | gtc | 912 |
| Glu | Val | Val | Gly | Gly | Val | Ser | Ile | Pro | Met | Ala | Ile | Leu | Phe | Gln | Val |
|     | 290 |     |     |     |     | 295 |     |     |     |     | 300 |     |     |     |      |
| ttc | gtg | ctg | ctc | gcc | acc | tgg | tcg | acc | aac | ccc | gca | gcg | aat | ctc | ctc | 960 |
| Phe | Val | Leu | Leu | Ala | Thr | Trp | Ser | Thr | Asn | Pro | Ala | Ala | Asn | Leu | Leu |
| 305 |     |     |     |     | 310 |     |     |     |     | 315 |     |     |     |     | 320 |
| tcg | ccg | gcg | tac | acg | ctg | tgc | agc | acg | ttc | ccg | cgg | gtg | ttc | acg | ttc | 1008 |
| Ser | Pro | Ala | Tyr | Thr | Leu | Cys | Ser | Thr | Phe | Pro | Arg | Val | Phe | Thr | Phe |
|     |     |     |     | 325 |     |     |     |     | 330 |     |     |     |     | 335 |      |
| aag | acc | ggt | gtg | atc | gtc | tcg | gcg | gtc | gtc | ggc | ctg | ctg | atg | atg | ccg | 1056 |
| Lys | Thr | Gly | Val | Ile | Val | Ser | Ala | Val | Val | Gly | Leu | Leu | Met | Met | Pro |
|     |     |     | 340 |     |     |     |     | 345 |     |     |     |     | 350 |     |      |
| tgg | cag | ttc | gcc | ggc | gtg | ctc | aac | acc | ttc | ctg | aac | ctg | ctt | gcg | agt | 1104 |
| Trp | Gln | Phe | Ala | Gly | Val | Leu | Asn | Thr | Phe | Leu | Asn | Leu | Leu | Ala | Ser |
|     |     |     | 355 |     |     |     |     | 360 |     |     |     |     | 365 |     |      |
| gct | ctc | ggc | ccg | ctc | gcg | ggg | atc | atg | atc | agc | gac | tac | ttc | ctc | gtg | 1152 |
| Ala | Leu | Gly | Pro | Leu | Ala | Gly | Ile | Met | Ile | Ser | Asp | Tyr | Phe | Leu | Val |
| 370 |     |     |     |     | 375 |     |     |     |     | 380 |     |     |     |     |      |
| cgc | cgt | cgc | cgc | atc | agc | ctg | cat | gac | ctg | tat | cgg | acc | aag | ggc | atc | 1200 |
| Arg | Arg | Arg | Arg | Ile | Ser | Leu | His | Asp | Leu | Tyr | Arg | Thr | Lys | Gly | Ile |
| 385 |     |     |     |     | 390 |     |     |     |     | 395 |     |     |     |     | 400 |
| tac | acg | tac | tgg | cga | ggg | gtc | aac | tgg | gtc | gca | ctc | gcg | gtc | tac | gcg | 1248 |
| Tyr | Thr | Tyr | Trp | Arg | Gly | Val | Asn | Trp | Val | Ala | Leu | Ala | Val | Tyr | Ala |
|     |     |     |     | 405 |     |     |     |     | 410 |     |     |     |     | 415 |      |
| gtc | gcg | ctg | gcg | gtg | tcg | ttc | ctc | act | ccg | gac | ctg | atg | ttc | gtg | acc | 1296 |
| Val | Ala | Leu | Ala | Val | Ser | Phe | Leu | Thr | Pro | Asp | Leu | Met | Phe | Val | Thr |
|     |     |     | 420 |     |     |     |     | 425 |     |     |     |     | 430 |     |      |
| ggc | ctg | atc | gcc | gcc | ctt | ctg | ctg | cac | atc | ccg | gcg | atg | cga | tgg | gtg | 1344 |
| Gly | Leu | Ile | Ala | Ala | Leu | Leu | Leu | His | Ile | Pro | Ala | Met | Arg | Trp | Val |
|     |     |     | 435 |     |     |     |     | 440 |     |     |     |     | 445 |     |      |
| gcg | aag | acc | ttc | ccg | ctg | ttc | tcc | gaa | gcc | gag | agc | cgg | aac | gag | gac | 1392 |
| Ala | Lys | Thr | Phe | Pro | Leu | Phe | Ser | Glu | Ala | Glu | Ser | Arg | Asn | Glu | Asp |
|     | 450 |     |     |     |     | 455 |     |     |     |     | 460 |     |     |     |      |
| tac | ctg | cga | ccg | atc | ggc | cct | gtg | gcg | ccg | gcg | gac | gaa | tca | gcg | act | 1440 |
| Tyr | Leu | Arg | Pro | Ile | Gly | Pro | Val | Ala | Pro | Ala | Asp | Glu | Ser | Ala | Thr |
| 465 |     |     |     |     | 470 |     |     |     |     | 475 |     |     |     |     | 480 |
| gcg | aac | acg | aag | gag | cag | aac | cag | cga | tga |     |     |     |     |     |     | 1470 |
| Ala | Asn | Thr | Lys | Glu | Gln | Asn | Gln | Arg |     |     |     |     |     |     |     |      |
|     |     |     |     | 485 |     |     |     |     |     |     |     |     |     |     |      |

<210> SEQ ID NO 2
<211> LENGTH: 489
<212> TYPE: PRT

<213> ORGANISM: microbacterium liquefaciens AJ3912

<400> SEQUENCE: 2

```
Met Ser Thr Thr Pro Ile Glu Glu Ala Arg Ser Leu Leu Asn Pro Ser
1               5                   10                  15

Asn Ala Pro Thr Arg Tyr Ala Glu Arg Ser Val Gly Pro Phe Ser Leu
            20                  25                  30

Ala Ala Ile Trp Phe Ala Met Ala Ile Gln Val Ala Ile Phe Ile Ala
        35                  40                  45

Ala Gly Gln Met Thr Ser Ser Phe Gln Val Trp Gln Val Ile Val Ala
    50                  55                  60

Ile Ala Ala Gly Cys Thr Ile Ala Val Ile Leu Leu Phe Phe Thr Gln
65                  70                  75                  80

Ser Ala Ala Ile Arg Trp Gly Ile Asn Phe Thr Val Ala Ala Arg Met
                85                  90                  95

Pro Phe Gly Ile Arg Gly Ser Leu Ile Pro Ile Thr Leu Lys Ala Leu
            100                 105                 110

Leu Ser Leu Phe Trp Phe Gly Phe Gln Thr Trp Leu Gly Ala Leu Ala
        115                 120                 125

Leu Asp Glu Ile Thr Arg Leu Leu Thr Gly Phe Thr Asn Leu Pro Leu
    130                 135                 140

Trp Ile Val Ile Phe Gly Ala Ile Gln Val Val Thr Thr Phe Tyr Gly
145                 150                 155                 160

Ile Thr Phe Ile Arg Trp Met Asn Val Phe Ala Ser Pro Val Leu Leu
                165                 170                 175

Ala Met Gly Val Tyr Met Val Tyr Leu Met Leu Asp Gly Ala Asp Val
            180                 185                 190

Ser Leu Gly Glu Val Met Ser Met Gly Gly Glu Asn Pro Gly Met Pro
        195                 200                 205

Phe Ser Thr Ala Ile Met Ile Phe Val Gly Gly Trp Ile Ala Val Val
    210                 215                 220

Val Ser Ile His Asp Ile Val Lys Glu Cys Lys Val Asp Pro Asn Ala
225                 230                 235                 240

Ser Arg Glu Gly Gln Thr Lys Ala Asp Ala Arg Tyr Ala Thr Ala Gln
                245                 250                 255

Trp Leu Gly Met Val Pro Ala Ser Ile Ile Phe Gly Phe Ile Gly Ala
            260                 265                 270

Ala Ser Met Val Leu Val Gly Glu Trp Asn Pro Val Ile Ala Ile Thr
        275                 280                 285

Glu Val Val Gly Gly Val Ser Ile Pro Met Ala Ile Leu Phe Gln Val
    290                 295                 300

Phe Val Leu Leu Ala Thr Trp Ser Thr Asn Pro Ala Ala Asn Leu Leu
305                 310                 315                 320

Ser Pro Ala Tyr Thr Leu Cys Ser Thr Phe Pro Arg Val Phe Thr Phe
                325                 330                 335

Lys Thr Gly Val Ile Val Ser Ala Val Val Gly Leu Leu Met Met Pro
            340                 345                 350

Trp Gln Phe Ala Gly Val Leu Asn Thr Phe Leu Asn Leu Leu Ala Ser
        355                 360                 365

Ala Leu Gly Pro Leu Ala Gly Ile Met Ile Ser Asp Tyr Phe Leu Val
    370                 375                 380

Arg Arg Arg Arg Ile Ser Leu His Asp Leu Tyr Arg Thr Lys Gly Ile
385                 390                 395                 400
```

```
Tyr Thr Tyr Trp Arg Gly Val Asn Trp Val Ala Leu Ala Val Tyr Ala
            405                 410                 415

Val Ala Leu Ala Val Ser Phe Leu Thr Pro Asp Leu Met Phe Val Thr
        420                 425                 430

Gly Leu Ile Ala Ala Leu Leu Leu His Ile Pro Ala Met Arg Trp Val
            435                 440                 445

Ala Lys Thr Phe Pro Leu Phe Ser Glu Ala Glu Ser Arg Asn Glu Asp
    450                 455                 460

Tyr Leu Arg Pro Ile Gly Pro Val Ala Pro Ala Asp Glu Ser Ala Thr
465                 470                 475                 480

Ala Asn Thr Lys Glu Gln Asn Gln Arg
            485

<210> SEQ ID NO 3
<211> LENGTH: 1506
<212> TYPE: DNA
<213> ORGANISM: Artificial
<220> FEATURE:
<223> OTHER INFORMATION: RGSH6
<220> FEATURE:
<221> NAME/KEY: CDS
<222> LOCATION: (1)..(1506)
<223> OTHER INFORMATION: RGSH6 tag

<400> SEQUENCE: 3
```

| | | | | | | | | | | | | | | | | |
|---|---|---|---|---|---|---|---|---|---|---|---|---|---|---|---|---|
| atg | aat | tcg | aca | ccc | atc | gaa | gag | gct | cgc | agc | ctc | ctg | aac | cca | tcc | 48 |
| Met | Asn | Ser | Thr | Pro | Ile | Glu | Glu | Ala | Arg | Ser | Leu | Leu | Asn | Pro | Ser | |
| 1 | | | | 5 | | | | | 10 | | | | | 15 | | |
| aat | gca | ccc | act | cga | tac | gcc | gag | cgc | tcc | gtc | ggc | ccg | ttc | tcc | ctc | 96 |
| Asn | Ala | Pro | Thr | Arg | Tyr | Ala | Glu | Arg | Ser | Val | Gly | Pro | Phe | Ser | Leu | |
| | | | 20 | | | | | 25 | | | | | 30 | | | |
| gcg | gcc | atc | tgg | ttc | gcc | atg | gcg | atc | cag | gtg | gcg | atc | ttc | atc | gcc | 144 |
| Ala | Ala | Ile | Trp | Phe | Ala | Met | Ala | Ile | Gln | Val | Ala | Ile | Phe | Ile | Ala | |
| | | 35 | | | | | 40 | | | | | 45 | | | | |
| gcg | gga | cag | atg | acg | agc | agc | ttc | cag | gtc | tgg | cag | gtg | atc | gtc | gcc | 192 |
| Ala | Gly | Gln | Met | Thr | Ser | Ser | Phe | Gln | Val | Trp | Gln | Val | Ile | Val | Ala | |
| | 50 | | | | | 55 | | | | | 60 | | | | | |
| atc | gcc | gca | ggc | tgc | acg | atc | gca | gtg | atc | ctg | ctc | ttc | ttc | acc | cag | 240 |
| Ile | Ala | Ala | Gly | Cys | Thr | Ile | Ala | Val | Ile | Leu | Leu | Phe | Phe | Thr | Gln | |
| 65 | | | | 70 | | | | | 75 | | | | | 80 | | |
| agc | gcg | gcg | atc | cgc | tgg | ggc | atc | aac | ttc | acg | gtc | gcc | gcg | cgg | atg | 288 |
| Ser | Ala | Ala | Ile | Arg | Trp | Gly | Ile | Asn | Phe | Thr | Val | Ala | Ala | Arg | Met | |
| | | | 85 | | | | | 90 | | | | | 95 | | | |
| cct | ttc | ggc | atc | cgc | gga | tcg | ctg | atc | ccg | atc | acc | ctc | aag | gcc | ctg | 336 |
| Pro | Phe | Gly | Ile | Arg | Gly | Ser | Leu | Ile | Pro | Ile | Thr | Leu | Lys | Ala | Leu | |
| | | | 100 | | | | | 105 | | | | | 110 | | | |
| ctc | tcg | ctg | ttc | tgg | ttc | ggc | ttc | cag | acg | tgg | ctg | ggc | gcg | ctg | gcg | 384 |
| Leu | Ser | Leu | Phe | Trp | Phe | Gly | Phe | Gln | Thr | Trp | Leu | Gly | Ala | Leu | Ala | |
| | | 115 | | | | | 120 | | | | | 125 | | | | |
| ctc | gat | gag | atc | acg | cgt | ctc | ctc | acc | gga | ttc | acg | aac | ctg | ccg | ctg | 432 |
| Leu | Asp | Glu | Ile | Thr | Arg | Leu | Leu | Thr | Gly | Phe | Thr | Asn | Leu | Pro | Leu | |
| | 130 | | | | | 135 | | | | | 140 | | | | | |
| tgg | atc | gtc | atc | ttc | ggc | gcg | atc | cag | gtc | gtg | acg | acc | ttc | tac | ggg | 480 |
| Trp | Ile | Val | Ile | Phe | Gly | Ala | Ile | Gln | Val | Val | Thr | Thr | Phe | Tyr | Gly | |
| 145 | | | | 150 | | | | | 155 | | | | | 160 | | |
| atc | acg | ttc | atc | cgc | tgg | atg | aac | gtc | ttc | gcc | tcg | ccg | gtg | ctc | ctc | 528 |
| Ile | Thr | Phe | Ile | Arg | Trp | Met | Asn | Val | Phe | Ala | Ser | Pro | Val | Leu | Leu | |
| | | | 165 | | | | | 170 | | | | | 175 | | | |
| gcg | atg | ggc | gtg | tac | atg | gtg | tac | ctg | atg | ctc | gac | ggc | gcc | gac | gtg | 576 |
| Ala | Met | Gly | Val | Tyr | Met | Val | Tyr | Leu | Met | Leu | Asp | Gly | Ala | Asp | Val | |
| | | | 180 | | | | | 185 | | | | | 190 | | | |

```
agc ctc ggc gag gtc atg tcg atg ggt ggc gag aac cct ggc atg ccg      624
Ser Leu Gly Glu Val Met Ser Met Gly Gly Glu Asn Pro Gly Met Pro
        195                 200                 205 ttc tcg acc gcg atc atg atc ttc gtc ggc ggc tgg atc gcg gtc gtg      672
Phe Ser Thr Ala Ile Met Ile Phe Val Gly Gly Trp Ile Ala Val Val
210                 215                 220 gtg agc atc cac gac atc gtg aag gag tgc aag gtc gac ccg aac gcg      720
Val Ser Ile His Asp Ile Val Lys Glu Cys Lys Val Asp Pro Asn Ala
225                 230                 235                 240 tcg cga gaa ggt cag acg aag gcc gac gcg cga tac gcc acg gcg cag      768
Ser Arg Glu Gly Gln Thr Lys Ala Asp Ala Arg Tyr Ala Thr Ala Gln
            245                 250                 255 tgg ctc ggc atg gtg ccg gca tcc atc atc ttc gga ttc atc ggc gcc      816
Trp Leu Gly Met Val Pro Ala Ser Ile Ile Phe Gly Phe Ile Gly Ala
        260                 265                 270 gcc tcg atg gtg ctg gtg ggg gag tgg aac ccg gtc atc gcc atc acc      864
Ala Ser Met Val Leu Val Gly Glu Trp Asn Pro Val Ile Ala Ile Thr
    275                 280                 285 gag gtg gtc ggc ggc gtg tcg atc ccg atg gcg atc ctc ttc cag gtc      912
Glu Val Val Gly Gly Val Ser Ile Pro Met Ala Ile Leu Phe Gln Val
290                 295                 300 ttc gtg ctg ctc gcc acc tgg tcg acc aac ccc gca gcg aat ctc ctc      960
Phe Val Leu Leu Ala Thr Trp Ser Thr Asn Pro Ala Ala Asn Leu Leu
305                 310                 315                 320 tcg ccg gcg tac acg ctg tgc agc acg ttc ccg cgg gtg ttc acg ttc     1008
Ser Pro Ala Tyr Thr Leu Cys Ser Thr Phe Pro Arg Val Phe Thr Phe
            325                 330                 335 aag acc ggt gtg atc gtc tcg gcg gtc gtc ggc ctg ctg atg atg ccg     1056
Lys Thr Gly Val Ile Val Ser Ala Val Val Gly Leu Leu Met Met Pro
        340                 345                 350 tgg cag ttc gcc ggc gtg ctc aac acc ttc ctg aac ctg ctt gcg agt     1104
Trp Gln Phe Ala Gly Val Leu Asn Thr Phe Leu Asn Leu Leu Ala Ser
    355                 360                 365 gct ctc ggc ccg ctc gcg ggg atc atg atc agc gac tac ttc ctc gtg     1152
Ala Leu Gly Pro Leu Ala Gly Ile Met Ile Ser Asp Tyr Phe Leu Val
370                 375                 380 cgc cgt cgc cgc atc agc ctg cat gac ctg tat cgg acc aag ggc atc     1200
Arg Arg Arg Arg Ile Ser Leu His Asp Leu Tyr Arg Thr Lys Gly Ile
385                 390                 395                 400 tac acg tac tgg cga ggg gtc aac tgg gtc gca ctc gcg gtc tac gcg     1248
Tyr Thr Tyr Trp Arg Gly Val Asn Trp Val Ala Leu Ala Val Tyr Ala
            405                 410                 415 gtc gcg ctg gcg gtg tcg ttc ctc act ccg gac ctg atg ttc gtg acc     1296
Val Ala Leu Ala Val Ser Phe Leu Thr Pro Asp Leu Met Phe Val Thr
        420                 425                 430 ggc ctg atc gcc gcc ctt ctg ctg cac atc ccg gcg atg cga tgg gtg     1344
Gly Leu Ile Ala Ala Leu Leu Leu His Ile Pro Ala Met Arg Trp Val
    435                 440                 445 gcg aag acc ttc ccg ctg ttc tcc gaa gcc gag agc cgg aac gag gac     1392
Ala Lys Thr Phe Pro Leu Phe Ser Glu Ala Glu Ser Arg Asn Glu Asp
450                 455                 460 tac ctg cga ccg atc ggc cct gtg gcg ccg gcg gac gaa tca gcg act     1440
Tyr Leu Arg Pro Ile Gly Pro Val Ala Pro Ala Asp Glu Ser Ala Thr
465                 470                 475                 480 gcg aac acg aag gag cag aac cag cct gca ggt ggt cgt ggc agc cac     1488
Ala Asn Thr Lys Glu Gln Asn Gln Pro Ala Gly Gly Arg Gly Ser His
            485                 490                 495 cat cac cac cac cat taa                                             1506
His His His His His
```

500

<210> SEQ ID NO 4
<211> LENGTH: 501
<212> TYPE: PRT
<213> ORGANISM: Artificial
<220> FEATURE:
<223> OTHER INFORMATION: RGSH6

<400> SEQUENCE: 4

Met Asn Ser Thr Pro Ile Glu Glu Ala Arg Ser Leu Leu Asn Pro Ser
1               5                   10                  15

Asn Ala Pro Thr Arg Tyr Ala Glu Arg Ser Val Gly Pro Phe Ser Leu
            20                  25                  30

Ala Ala Ile Trp Phe Ala Met Ala Ile Gln Val Ala Ile Phe Ile Ala
        35                  40                  45

Ala Gly Gln Met Thr Ser Ser Phe Gln Val Trp Gln Val Ile Val Ala
    50                  55                  60

Ile Ala Ala Gly Cys Thr Ile Ala Val Ile Leu Leu Phe Phe Thr Gln
65                  70                  75                  80

Ser Ala Ala Ile Arg Trp Gly Ile Asn Phe Thr Val Ala Ala Arg Met
                85                  90                  95

Pro Phe Gly Ile Arg Gly Ser Leu Ile Pro Ile Thr Leu Lys Ala Leu
            100                 105                 110

Leu Ser Leu Phe Trp Phe Gly Phe Gln Thr Trp Leu Gly Ala Leu Ala
        115                 120                 125

Leu Asp Glu Ile Thr Arg Leu Leu Thr Gly Phe Thr Asn Leu Pro Leu
    130                 135                 140

Trp Ile Val Ile Phe Gly Ala Ile Gln Val Val Thr Thr Phe Tyr Gly
145                 150                 155                 160

Ile Thr Phe Ile Arg Trp Met Asn Val Phe Ala Ser Pro Val Leu Leu
                165                 170                 175

Ala Met Gly Val Tyr Met Val Tyr Leu Met Leu Asp Gly Ala Asp Val
            180                 185                 190

Ser Leu Gly Glu Val Met Ser Met Gly Gly Glu Asn Pro Gly Met Pro
        195                 200                 205

Phe Ser Thr Ala Ile Met Ile Phe Val Gly Gly Trp Ile Ala Val Val
    210                 215                 220

Val Ser Ile His Asp Ile Val Lys Glu Cys Lys Val Asp Pro Asn Ala
225                 230                 235                 240

Ser Arg Glu Gly Gln Thr Lys Ala Asp Ala Arg Tyr Ala Thr Ala Gln
                245                 250                 255

Trp Leu Gly Met Val Pro Ala Ser Ile Ile Phe Gly Phe Ile Gly Ala
            260                 265                 270

Ala Ser Met Val Leu Val Gly Glu Trp Asn Pro Val Ile Ala Ile Thr
        275                 280                 285

Glu Val Val Gly Gly Val Ser Ile Pro Met Ala Ile Leu Phe Gln Val
    290                 295                 300

Phe Val Leu Leu Ala Thr Trp Ser Thr Asn Pro Ala Ala Asn Leu Leu
305                 310                 315                 320

Ser Pro Ala Tyr Thr Leu Cys Ser Thr Phe Pro Arg Val Phe Thr Phe
                325                 330                 335

Lys Thr Gly Val Ile Val Ser Ala Val Val Gly Leu Leu Met Met Pro
            340                 345                 350

Trp Gln Phe Ala Gly Val Leu Asn Thr Phe Leu Asn Leu Leu Ala Ser

```
                355                 360                 365
Ala Leu Gly Pro Leu Ala Gly Ile Met Ile Ser Asp Tyr Phe Leu Val
        370                 375                 380

Arg Arg Arg Arg Ile Ser Leu His Asp Leu Tyr Arg Thr Lys Gly Ile
385                 390                 395                 400

Tyr Thr Tyr Trp Arg Gly Val Asn Trp Val Ala Leu Ala Val Tyr Ala
                405                 410                 415

Val Ala Leu Ala Val Ser Phe Leu Thr Pro Asp Leu Met Phe Val Thr
            420                 425                 430

Gly Leu Ile Ala Ala Leu Leu Leu His Ile Pro Ala Met Arg Trp Val
            435                 440                 445

Ala Lys Thr Phe Pro Leu Phe Ser Glu Ala Glu Ser Arg Asn Glu Asp
            450                 455                 460

Tyr Leu Arg Pro Ile Gly Pro Val Ala Pro Ala Asp Glu Ser Ala Thr
465                 470                 475                 480

Ala Asn Thr Lys Glu Gln Asn Gln Pro Ala Gly Gly Arg Gly Ser His
                485                 490                 495

His His His His His
            500

<210> SEQ ID NO 5
<211> LENGTH: 32
<212> TYPE: DNA
<213> ORGANISM: Artificial
<220> FEATURE:
<223> OTHER INFORMATION: pSHP11H-5'

<400> SEQUENCE: 5
cgtcaatgaa ttcgacaccc atcgaagagg ct                              32

<210> SEQ ID NO 6
<211> LENGTH: 33
<212> TYPE: DNA
<213> ORGANISM: Artificial
<220> FEATURE:
<223> OTHER INFORMATION: pSHP11H-3'

<400> SEQUENCE: 6
tccttctcct gcagggtact gcttctcggt ggg                             33

<210> SEQ ID NO 7
<211> LENGTH: 10
<212> TYPE: PRT
<213> ORGANISM: Artificial
<220> FEATURE:
<223> OTHER INFORMATION: MHPH6 N end

<400> SEQUENCE: 7

Met Asn Ser Thr Pro Ile Glu Glu Ala Arg
1               5                   10
```